United States Patent
Choi et al.

(10) Patent No.: US 12,133,891 B2
(45) Date of Patent: Nov. 5, 2024

(54) MICROBUBBLE-EXTRACELLULAR VESICLE COMPLEXES

(71) Applicants: Industry Foundation of Chonnam National University, Gwangju (KR); Korea Institute of Medical Mcrorobotics, Gwangju (KR); Johns Hopkins University, Baltimore, MD (US)

(72) Inventors: Eun Pyo Choi, Gwangju (KR); Jong Oh Park, Gyeonggi-do (KR); Chang Sei Kim, Gwangju (KR); You Hee Choi, Gwangju (KR); Byung Jeon Kang, Gwangju (KR); Ho Yong Kim, Gwangju (KR); Hyeong Woo Song, Jeollanam-do (KR); Dae Won Jung, Gwangju (KR); Han Sol Lee, Gyeonggi-do (KR); Deok Ho Kim, Ellicott City, MD (US); Min Jae Do, Baltimore, MD (US)

(73) Assignees: INDUSTRY FOUNDATION OF CHONNAM NATIONAL UNIVERSITY, Gwangju (KR); KOREA INSTITUTE OF MEDICAL MICROROBOTICS, Gwangju (KR); Johns Hopkins University, Baltimore, MD (US)

(*) Notice: Subject to any disclaimer, the term of this patent is extended or adjusted under 35 U.S.C. 154(b) by 120 days.

(21) Appl. No.: 17/517,621

(22) Filed: Nov. 2, 2021

(65) Prior Publication Data
US 2023/0136448 A1 May 4, 2023

(51) Int. Cl.
*A61K 47/69* (2017.01)
*A61K 41/00* (2020.01)
*A61K 47/64* (2017.01)
*A61N 7/00* (2006.01)

(52) U.S. Cl.
CPC .......... *A61K 41/0028* (2013.01); *A61K 47/64* (2017.08); *A61K 47/6911* (2017.08); *A61N 2007/0078* (2013.01)

(58) Field of Classification Search
None
See application file for complete search history.

(56) References Cited

U.S. PATENT DOCUMENTS

| 8,226,538 B2 * | 7/2012 | Liu | A61N 7/02 600/407 |
| 2017/0080114 A1 * | 3/2017 | Kim | A61K 9/5169 |
| 2020/0187981 A1 * | 6/2020 | Tian | A61B 8/0841 |

OTHER PUBLICATIONS

Yan F, Li L, Deng Z, Jin Q, Chen J, Yang W, Yeh CK, Wu J, Shandas R, Liu X, Zheng H. Paclitaxel-liposome-microbubble complexes as ultrasound-triggered therapeutic drug delivery carriers. Journal of controlled release. Mar. 28, 2013;166(3):246-55. (Year: 2013).*
Liao W, Du Y, Zhang C, Pan F, Yao Y, Zhang T, Peng Q. Exosomes: the next generation of endogenous nanomaterials for advanced drug delivery and therapy. Acta biomaterialia. Mar. 1, 2019;86:1-4. (Year: 2019).*
Otani K, Yamahara K. Development of antibody-carrying microbubbles based on clinically available ultrasound contrast agent for targeted molecular imaging: a preliminary chemical study. Molecular Imaging and Biology. Apr. 2011;13:250-6. (Year: 2011).*
Diaz G, Wolfe LM, Kruh-Garcia NA, Dobos KM. Changes in the membrane-associated proteins of exosomes released from human macrophages after Mycobacterium tuberculosis infection. Scientific reports. Nov. 29, 2016;6(1):37975. (Year: 2016).*
Altanerova U, Jakubechova J, Benejova K, Priscakova P, Pesta M, Pitule P, Topolcan O, Kausitz J, Zduriencikova M, Repiska V, Altaner C. Prodrug suicide gene therapy for cancer targeted intracellular by mesenchymal stem cell exosomes. International journal of cancer. Feb. 15, 2019;144(4):897-908. (Year: 2019).*
Fan CH, Cheng YH, Ting CY, Ho YJ, Hsu PH, Liu HL, Yeh CK. Ultrasound/magnetic targeting with SPIO-DOX-microbubble complex for image-guided drug delivery in brain tumors. Theranostics. 2016;6(10):1542. (Year: 2016).*
Farcas M, Inngjerdingen M. Natural killer cell-derived extracellular vesicles in cancer therapy. Scandinavian journal of immunology. Oct. 2020;92(4):e12938. (Year: 2020).*
CaroBull JL. The application of microbubbles for targeted drug delivery. Expert opinion on drug delivery. Sep. 1, 2007;4(5):475-93. (Year: 2007).*

* cited by examiner

*Primary Examiner* — Nissa M Westerberg
(74) *Attorney, Agent, or Firm* — Harness, Dickey & Pierce, P.L.C.

(57) ABSTRACT

Disclosed herein are a microbubble-extracellular vesicle complex, a production method therefor, and a system for driving the same. In one aspect, preferred microbubble-extracellular vesicle complexes may comprise an ultrasound contrast agent-based microbubble, an extracellular cell derived from a natural killer cell (NK cell), a human glial cell, or a human mesenchymal stem cell, and a coupling medium and can be derive in a 3D mode using ultrasonic waves and deliver a drug loaded in the extracellular vesicle to a target site.

1 Claim, 31 Drawing Sheets

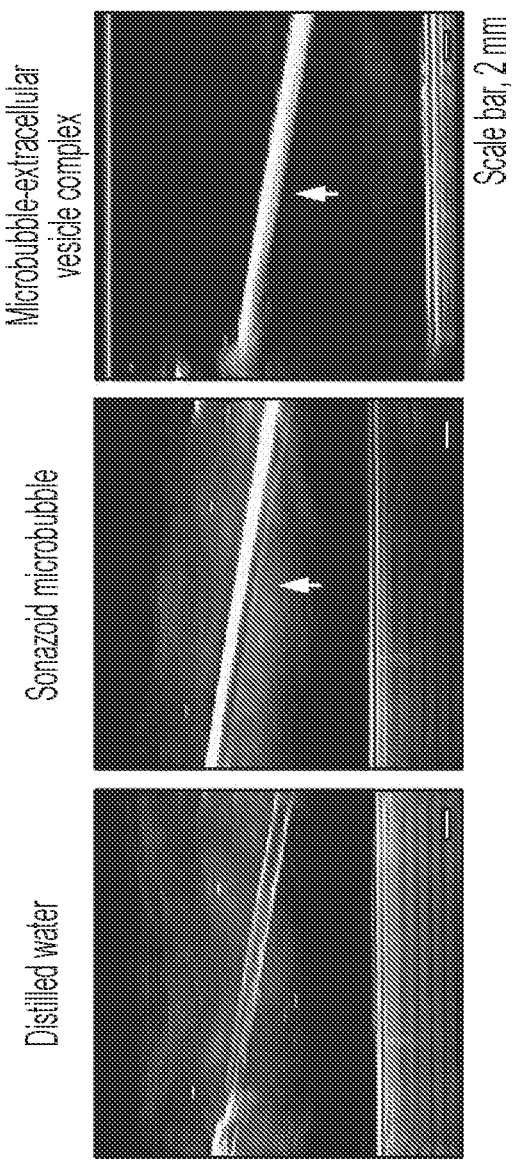
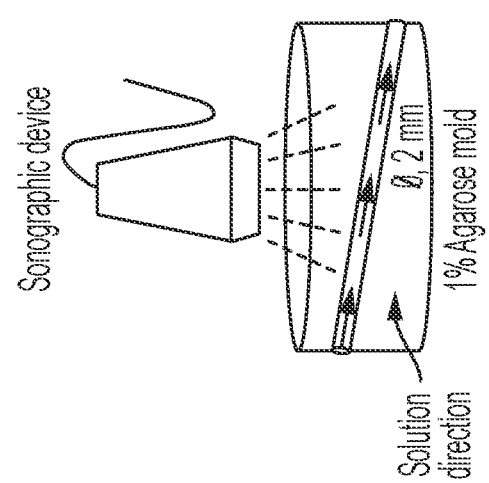
FIG. 6B
FIG. 6A

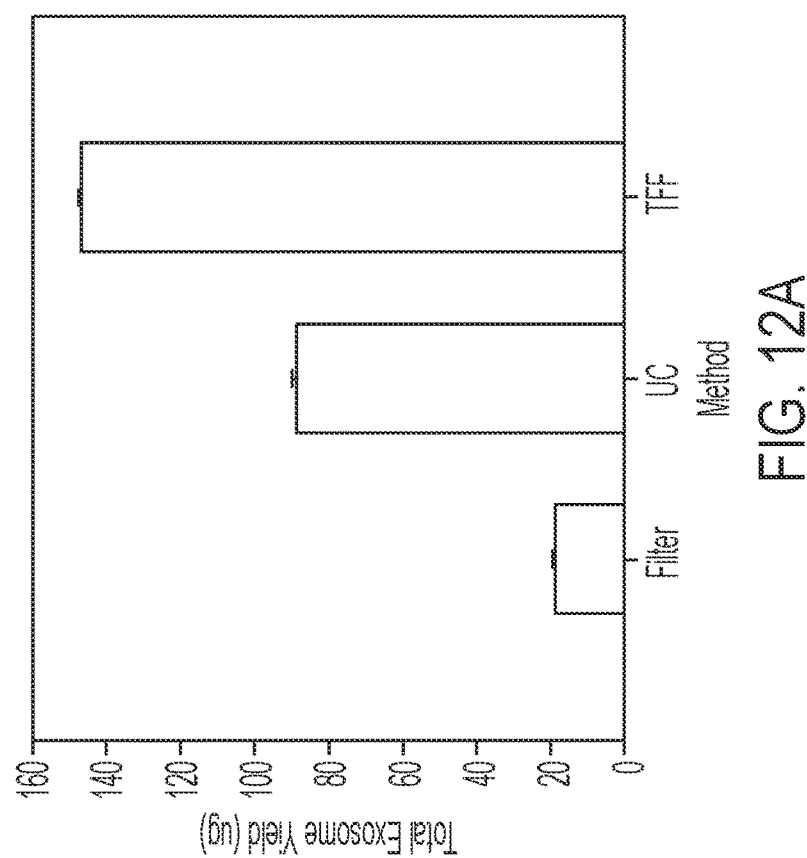
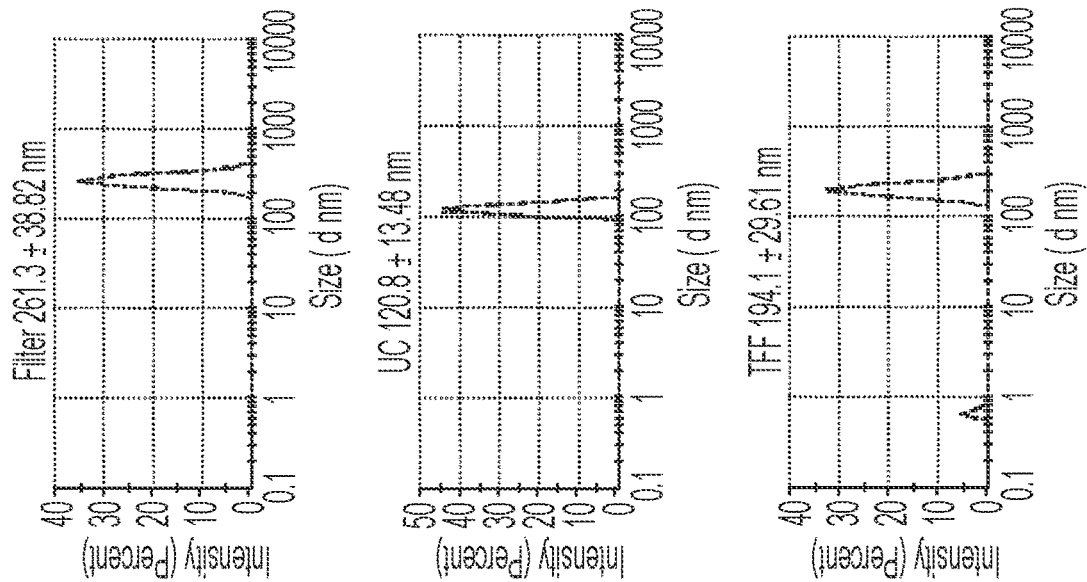
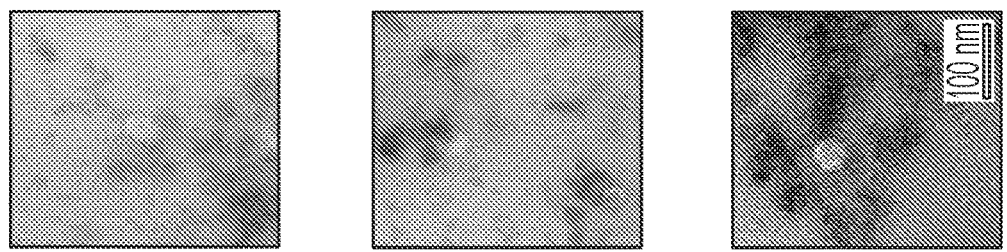
FIG. 12A
FIG. 12B
FIG. 12C

MICROBUBBLE-EXTRACELLULAR VESICLE COMPLEXES

BACKGROUND

Field

The present disclosure relates to a microbubble-extracellular vesicle complex, a production method therefor, and a system for driving the same, wherein the microbubble-extracellular vesicle complex comprises an ultrasound contrast agent-based microbubble, an extracellular cell derived from a natural killer cell (NK cell), a human glial cell, or a human mesenchymal stem cell, and a coupling medium and can be derive in a 3D mode using ultrasonic waves and deliver a drug loaded in the extracellular vesicle to a target site.

Background

Microbubbles, which are structured to envelop the bio-inert gas perfluorocarbons (PFCs) with a phospholipid membrane, have been used as an ultrasound contrast agent for about 30 years in the diagnostic medicine field. After administration of an ultrasound contrast agent, ultrasonic application allows clearer images of internal organs as the ultrasonic waves are reflected by the microbubbles within the contrast agent.

Ultrasound contrast agents have been advanced since 1968 when Gramiak and Shah discovered augmented ultrasonic signals after injection microbubbles into blood vessels. Examples of the contrast agents known up to now include small air bubbles enclosed by gelatin shells; small gaseous bodies having polysaccharide solid peripheral walls; small air bubbles using particulates of solid crystalline compounds; small air bubbles using fatty acids; and small air bubbles prepared by using fatty acids and surfactants.

In recent years, trials have been made to develop theragnostic agents capable of simultaneously conducting diagnosis and therapy by conjugating liposomes having drugs, DNAs, or proteins loaded therein to the surface of such ultrasound contrast agents.

The term "theragnostic agent" refers generally to a substance that makes diagnosis and therapy of a disease possible at the same time. Usually, a theragnostic agent is made of small-sized materials and has a structure in which a liposome, a polymer, or a nanoparticle has a fluorescent dye or radioactive molecule loaded therein and a drug or diagnostic marker introduced on the outside thereof.

The synthesis of theragnostic agents having lipid structures of high biocompatibility has been predominantly studied. Inter alia, active research has been conducted into bioimaging analysis using a microbubble ultrasound agent, which is a micron-sized, air bubble ultrasound agent having a lipid structure. These studies have recently been focused on impartment of characteristics, such as non-toxicity, high water solubility, easy surface modification, and so on, in order to apply nanomaterials to biology-relevant fields called "nano-bio fields".

However, theragnostic agents employing liposomes as carriers suffer from various problems in that liposomes on the surface exhibit cytotoxicity, the treatment of affected cells by delivering a therapeutic substance thereto in a target specific manner is restricted, and the like.

In addition, liposomes are difficult to apply to the medical field due to the low immune compatibility thereof and cannot effectively deliver therapeutic substances due to lack of pertinent bundling ability.

Therefore, there is an urgent need for development of a novel drug delivery carrier that is free of cytotoxicity and immunogenicity and can effectively deliver a therapeutic substance with an enhanced targeting ability.

SUMMARY

We now provide complexes that comprise 1) one or more microbubbles and 2) one or more extracellular vesicles associated with the one or more microbubbles.

Preferred complexes include those where a microbubble contacts the extracellular vesicle, for example the extracellular vesicle may be loaded with one or more microbubbles.

In particular aspects, the microbubble and the extracellular vesicle are covalently linked. In certain aspects, the microbubble may comprises a first linker group and the extracellular vesicle may comprises second linker group, and the first and second linker groups are coupled such as through one or more covalent bonds.

In one aspect, a complex is provided that comprises microbubbles and extracellular vesicles, where the complex is at least substantially free of cytotoxicity and immunogenicity in vivo.

In preferred systems, the complex can be driven with an ultrasound transducer. Suitably, the complex can effectively deliver a therapeutic substance to a target site.

In preferred aspects, a microbubble-extracellular vesicle complex is provided comprising an ultrasound contrast agent-based microbubble, an extracellular vesicle derived from a natural killer cell (NK cell), a human glial cell, or a human mesenchymal stem cell, and a coupling medium is at least substantially free of cytotoxicity and immunogenicity in vivo. Preferably, the complex can be driven in a three-dimensional mode by an ultrasonic driving device. Preferably, the complex can effectively deliver a drug loaded to the extracellular vesicle to a target site.

Therefore, an aspect of the present disclosure is to provide a microbubble-extracellular vesicle complex.

Another aspect of the present disclosure is to provide a method for production of a microbubble-extracellular vesicle complex.

A further aspect of the present disclosure is to provide a pharmaceutical composition comprising a microbubble-extracellular vesicle complex as disclosed herein, including as an active ingredient.

A further aspect of the present disclosure is to provide a method for delivering drug loaded in the extracellular vesicle to a target site.

A yet another aspect of the present disclosure is to provide a driving system for a microbubble-extracellular vesicle complex.

In certain aspects, a microbubble-extracellular vesicle complex may have a diameter or longest dimension of from 0.3 μm or 0.5 to 10 μm or more; or from 0.5 to 8 μm or 10 μm or more; or from 0.5 or 0.8 μm to 3, 4, 5, 6, 7, 8, 9 or 10 μm or more.

Certain microbubble systems are disclosed in WO2020138886; U.S. Pat. No. 9,375,397; WO2010/

133700; and US 2017/0007546, each of which are incorporated herein in their entirety.

Other aspects are disclosed infra.

BRIEF DESCRIPTION OF THE DRAWINGS

The above and other aspects, features and advantages of the present disclosure will be more apparent from the following detailed description taken in conjunction with the accompanying drawings, in which:

FIG. 6 (includes 6A-6B) shows ultrasonic images of the microbubbles and the microbubble-extracellular vesicle complex.

FIG. 10 (includes FIGS. 10A-10E).

FIG. 11 (includes FIGS. 11A-11B).

FIG. 12 (includes FIGS. 12A-12C). Development of exosome carrier acquisition method for enhanced yield.

DETAILED DESCRIPTION

Figure 1:
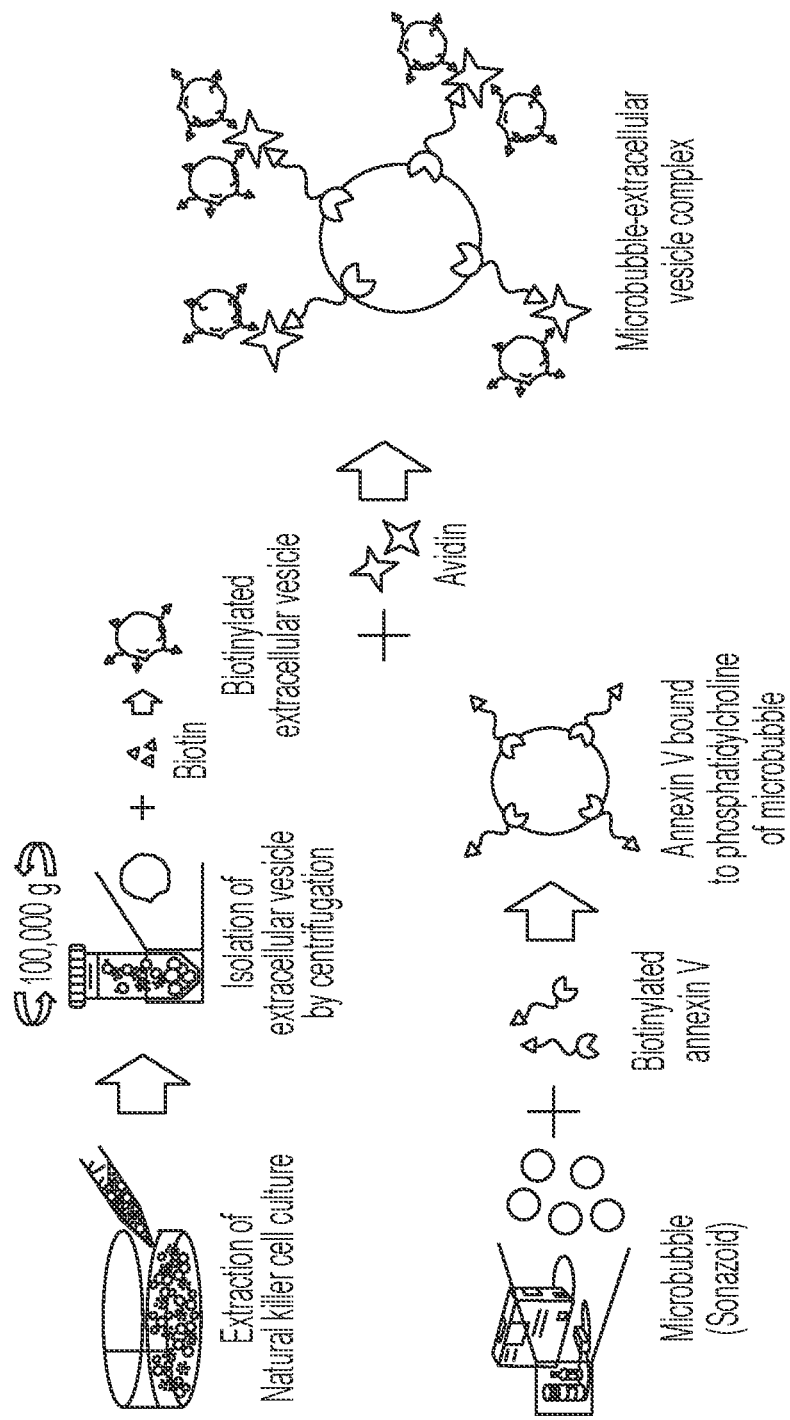
FIG. 1 is a conceptual diagram illustrating an overall procedure for fabricating a microbubble-extracellular vesicle complex according to a preparation embodiment of the present disclosure.

As discussed, in various aspects, we now provide a microbubble-extracellular vesicle complex comprising a microbubble, an extracellular vesicle, and a coupling medium, a production method therefor, and a driving system therefor and, more specifically, to a microbubble-extracellular vesicle complex in which a microbubble and a drug-loaded extracellular vesicle are coupled to each other, whereby the microbubble-extracellular vesicle is at least substantially free of cytotoxicity and immunogenicity in vivo and preferably can deliver the drug to a target site and be driven with ultrasound, a production method therefor, and a driving system therefor.

In a preferred system, being able to be driven in a three-dimensional mode, the microbubble-extracellular vesicle complex comprising a microbubble, a natural killer cell (NK cell)-derived extracellular vesicle, and a coupling medium according to the present disclosure can effectively deliver one or more drugs loaded in the extracellular vesicle to a target site, without cytotoxicity and immunogenicity in vivo.

An aspect of the present disclosure is concerned with a microbubble-extracellular vesicle complex comprising: a microbubble comprising a first linker and bonded with a first anchor; and an extracellular vesicle comprising a second linker and bonded with a second anchor, wherein the first linker and the second linker are coupled to each other.

In the present disclosure, the microbubble may comprise a first linker and be bonded with a first anchor.

In the present disclosure, the first linker may be capable of being coupled to a different linker.

Coupling between linkers can be made by click chemistry without a separate coupling medium.

In the present disclosure, the first linker may include at least one selected from the group consisting of biotin, thiol, amine, aldehyde, sulfide, imide, alcohol, carboxyl, carbonyl, succinimide, maleimide, epoxide, azide, alkyne, isocyanate, genipin, pyridyldithiol, multifunctional maleimide, diimidoester, polyimidoester, bis-diazonium, n-hydroxysuccinimideester, haloacetyl, chitosan, poly(ethylenimine), poly L-lysine, polydiallyldimethyl ammonium chloride, polyallylamine, hydrochloride, poly-omithine, polyvinylamine hydrochloride, poly (2-(dimethylamino)ethyl methacrylate), polyamido amine, polypropylenimine, polyamidoamine, dendrimer, and gelatin, for example, biotin, but with no limitations thereto.

In an embodiment of the present disclosure, the first linker may include a lipid.

In the present disclosure, the lipid may be at least one selected from a natural phospholipid, a hydrogenated product of a natural phospholipid, a synthetic phospholipid, a derivative of a synthetic phospholipid, and a fatty acid mixture obtained by hydrolysis of a synthetic phospholipid, for example, may be a natural phospholipid, but with no limitations thereto.

In the present disclosure, the natural phospholipid may be at least one selected from the group consisting of phosphatidylcholine, soybean lecithin, lysolecithin, sphingomyelin, phosphatidic acid, phosphatidylserine, phosphatidylglycerol, phosphatidylinositol, phosphatidylethanolamine, and cardiolipin, for example, phosphatidylcholine, but is not limited thereto.

In the present disclosure, the synthetic phospholipid may be at least one selected from the group consisting of dicetyl phosphate, distearoyl phosphatidylcholine, dioleoyl phosphatidylethanolamine, dipalmitoyl phosphatidylcholine, dipalmitoyl phosphatidylethanolamine, dipalmitoyl phosphatidylserine, eleostearoyl phosphatidylcoline, eleostearoyl phosphatidylethanolamine, and eleostearoyl phosphatidylserine, but with no limitations thereto.

In the present disclosure, the first anchor may function to mediate conjugation between the first linker and the microbubble.

In the present disclosure, the first anchor may be at least one selected from the group consisting of Annexin V, Tenascin-N, transferrin receptor protein 1, glucose transporter 1, complement C9, CD88 antigen, α-1-acidic glycoprotein, matrix metalloprotease 9, angiopoietin-1, CD67 antigen, mucin-5B, GRB2 adaptor protein, olfactomedin-4, neutral amino acid transporter B(0), tripeptidyl peptidase 1, heat shock-related 70 kDa protein 2, proteasome subunit α type-5 and neutrophil gelatinase-associated lipocalin, N-azidoacetyl mannosamine, N-azidoacetyl galactosamine, N-azidoacetyl glucosamine, 6-azidofucose, and lysosome-associated membrane protein 2 (LAMP2), for example, annexin V, but with no limitations thereto.

In the present disclosure, the microbubble may be at least one selected from the group consisting of a gas-filled microsphere, a gas-filled liposome, and a gas-forming emulsion, for example, a gas-filled liposome, but with no limitations thereto.

In the present disclosure, the microbubble may contain a gas therein, but with no limitations thereto.

In the present disclosure, the gas may be, but is not limited to, a perfluocarbon compound of 1 to 6 carbon atoms.

In the present disclosure, a volume ratio (v/v %) of the microbubble and the first anchor may be of 1:0.001 to 0.500, 1:0.001 to 0.4000, 1:0.001 to 0.300, 1:0.001 to 0.250, 1:0.001 to 0.200, 1:0.001 to 0.100, 1:0.010 to 0.500, 1:0.010 to 0.400, 1:0.010 to 0.300, 1:0.010 to 0.250, 1:0.010 to 0.200, 1:0.010 to 0.100, 1:0.050 to 0.500, 1:0.050 to 0.400, 1:0.050 to 0.300, 1:0.050 to 0.250, 1:0.050 to 0.200, or 1:0.050 to 0.100, for example, 1:0.050 to 0.100, but with no limitations thereto.

In the present disclosure, the extracellular vesicle may comprise a second linker and be bonded with a second anchor.

In an embodiment of the present disclosure, the second linker may comprise a lipid.

In the present disclosure, the second linker may be at least one selected from the group consisting of biotin, thiol, amine, aldehyde, sulfide, imide, alcohol, carboxyl, carbonyl, succinimide, maleimide, epoxide, azide, alkyne, isocyanate, genipin, pyridyldithiol, multifunctional maleimide, diimidoester, polyimidoester, bis-diazonium, n-hydroxysuccinimideester, haloacetyl, chitosan, poly(ethylenimine), poly L-lysine, polydiallyldimethyl ammonium chloride, polyallylamine, hydrochloride, poly-omithine, polyvinylamine hydrochloride, poly (2-(dimethylamino)ethyl methacrylate), polyamido amine, polypropylenimine, polyamidoamine, dendrimer, and gelatin, for example, biotin, but with no limitations thereto.

In the present disclosure, the second anchor may be bonded to the second linker.

In the present disclosure, the second anchor may function to mediate conjugation between the second linker and the extracellular vesicle.

In the present disclosure, the second anchor may be at least one selected from the group consisting of sulfo-NHS (N-hydroxysulfosuccinimide), NHS (N-hydroxysuccinimide), pyridyl disulfide, amine, acetylmannosamine, acetylgalactosamine, acetylglucosamine, azidofucose, maleimide, succinimide, isothiocyanate, pyridyldithiol, halo acetyl, difluoro, genipin, antibodies, nanobodies, peptides, and aptamers, for example, sulfo-NHS, but with no limitations thereto.

In the present disclosure, the extracellular vesicle may be at least one selected from the group consisting of an exosome, an apoptotic body, and a macrovesicle (ectosome), for example, exosome, but with no limitations thereto.

In the present disclosure, the extracellular vesicle may be derived from at least one selected from the group consisting of a natural killer cell (NK cell), a natural killer-like cell, an astrocyte, an oligodendrocyte, an ependymal cell, a radial glia, a Schwann cell, and a mesenchymal stem cell, for example, a natural killer cell, but with no limitations thereto.

Extracellular vesicles secreted from natural killer cells are as small as 50 to 150 nm in size and are known to easily circulate in vivo and be free of self-replication and cytotoxicity. Taking advantage of these characteristics, the nano-sized, natural killer cell-derived extracellular vesicles succeeding to the genetic materials and information that natural killer cells retain can be used to improve efficiency of targeting to desired cancer sites and enhance anticancer immunity, thereby augmenting cancer cell killer effects.

Neuroglia exist proximal to neuronal cells in the body, surrounding the motor nervous system and sensory nervous system in the vicinity of the central nervous system and the peripheral nervous system. As important cells that allow neuronal cells to maintain homeostasis through metabolic exchange, neuroglia play a critical role in recovering nerve tissues which have been damaged. Examples of neuroglia include astrocytes, oligodendrocytes, ependymal cells, radial glia, and Schwann cells. When troubled, neuroglia have difficulty in maintaining homeostasis, giving rise to various neuropathies.

Mesenchymal stem cells, which are known to have therapeutic effects, can be generally employed as a source for the extracellular vesicle.

In the present disclosure, the extracellular vesicle may range in diameter from 20 to 250 nm, from 20 to 200 nm, from 20 to 150 nm, from 30 to 250 nm, from 30 to 200 nm, or 30 to 150 nm, for example, from 30 to 150 nm.

In the present disclosure, the extracellular vesicle may load various substances, such as a DNA, a RNA, a protein, a recombinant protein, an anticancer protein, a tumor suppressor gene, and an anticancer compound, therein, but with no limitations thereto.

In the present disclosure, the anticancer protein may be at least one selected from the group consisting of asparaginase, botulinum toxin, tetanus toxin, Shiga toxin, diphtheria toxin (DT), ricin, pseudomonas exotoxin (PE), cytolysin A (ClyA), γ-gelonin, VEGF (vascular endothelial growth factor), angiopoietin 1 (Ang 1), angiopoietin 2 (Ang 2), transforming growth factor-β (TGF-β), integrin, vascular endothelial-cadherin (VE-cadherin), plasminogen activator (PA), ephrin, platelet-derived growth factor (PDGF), monocyte chemotactic protein-1 (MCP-1), fibroblast growth factor (FGF), placenta growth factor (PlGF), APC (adenomatous polyposis coli), CD95 (cluster of differentiation 95), ST5 (suppression of tumorigenicity 5), YPEL3 (Yippee like 3), ST7 (suppression of tumorigenicity 7), and ST14 (suppression of tumorigenicity 14), but with no limitations thereto.

In the present disclosure, the tumor suppressor gene may be at least one selected from the group consisting of VHL (Von HippelLindau), APC (adenomatous polyposis coli), CD95 (cluster of differentiation 95), ST5 (suppression of tumorigenicity 5), YPEL3 (Yippee like 3), ST7 (suppression of tumorigenicity 7), and ST14 (suppression of tumorigenicity 14), but with no limitations thereto.

In the present disclosure, the anticancer compound may be at least one selected from the group consisting of methotrexate, 5-fluorouracil, gemcitabine, arabinosylcytosine, hydroxy urea, mercaptopurine, thioguanine, nitrogen mustard, cyclosporamide, anthracycline, daunorubicin, doxorubicin, epirubicin, idarubicin, pixantrone, sabarubicin, valrubicin, actinomycin D, vincristine, taxol, combretastatin A4, fumagillin, herbimycin A, 2-methoxyestradiol, OGT 2115, TNP 470, tranilast, XRP44X, thalidomide, endostatin, salmosin, angiostatin, plasminogen, Kringle domain in apolipoprotein, oxaliplatin, carboplatin, cisplatin, bortezomib, and radionuclides, but is not limited thereto.

In an embodiment of the present disclosure, the microbubble-extracellular vesicle complex may further comprise a coupling medium.

In an embodiment of the present disclosure, the coupling medium may mediate coupling between the first linker and the second linker.

In an embodiment of the present disclosure, the coupling medium may be a protein.

In an embodiment of the present disclosure, the coupling medium may mediate coupling between the first linker and the second linker through protein interaction.

In the present disclosure, coupling medium may be at least one selected from the group consisting of avidin, streptavidin, neutravidin, and captavidin, for example, avidin, but with no limitations thereto.

In an embodiment of the present disclosure, the avidin, which is basically charged glycoprotein, can bind one or more biotin molecules through avidin-biotin complex technique.

Another aspect of the present disclosure contemplates a method for producing a microbubble-extracellular vesicle complex, the method comprising:

a first mixing step of mixing a first microstructure with a microbubble to prepare a first mixture;

a second mixing step of mixing a second microstructure with an extracellular vesicle to prepare a second mixture; and a third mixing step of mixing the first mixture and the second mixture.

In the present disclosure, the first mixing step may be carried out by mixing a first microstructure with a microbubble to prepare a first mixture.

In the present disclosure, the first microstructure may comprise a first linker and a first anchor.

According to the present disclosure, the first linker in the first microstructure may be conjugated with the first anchor via a lipid.

In an embodiment of the present disclosure, the first microstructure may be biotinylated annexin V.

In an embodiment of the present disclosure, the first mixture may contain biotinylated annexin V and a microbubble.

In the present disclosure, the second mixing step may be carried out by mixing a second microstructure and an extracellular vesicle to prepare a second mixture.

In the present disclosure, the second microstructure may comprise a second linker and a second anchor.

According to the present disclosure, the second linker in the second microstructure may be conjugated with the second anchor via a lipid.

In an embodiment of the present disclosure, the second microstructure may be a sulfo-NHS-conjugated biotin.

In an embodiment of the present disclosure, the second mixture may contain a biotinylated extracellular vesicle.

In the present disclosure, the first mixing step and the second mixing step may each be independently conducted irrespective of the order thereof. By way of example, the first mixing step may be carried out prior to, subsequent to, or simultaneously with the second mixing step.

In an embodiment of the present disclosure, the first mixing step may further comprise a medium mixing step of mixing the first mixture with a coupling medium.

Through this procedure, an improvement can be brought about in convenience of mixing and yield upon the production of a microbubble-extracellular vesicle complex.

In the present disclosure, the third mixing step may be set to mix the first mixture and the second mixture.

A further aspect of the present disclosure is concerned with a pharmaceutical composition comprising the microbubble-extracellular vesicle complex as an active ingredient.

A further aspect of the present disclosure is to provide a method for delivering drug loaded in the extracellular vesicle to a target site may comprises administering to a subject a composition comprising a microbubble-extracellular vesicle complex as an active ingredient;

moving the microbubble-extracellular vesicle complex by applying ultrasonic waves to the surroundings of the complex to form a focal point and changing the position of the focal point.

In the present disclosure, the composition comprising a microbubble-extracellular vesicle complex as an active ingredient may comprise a pharmaceutically acceptable carrier, but with no limitations thereto.

In the present disclosure, the pharmaceutically acceptable carrier may be one usually used for formulations and includes, but is not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil.

In the present disclosure, the pharmaceutically acceptable carrier may further comprise a lubricant, a humectant, a sweetener, a flavorant, an emulsifier, a preservative, or a combination thereof, but with no limitations thereto.

A still another aspect of the present disclosure pertains to a microbubble-extracellular vesicle complex driving system, comprising: a plurality of ultrasonic transducers; and a microbubble-extracellular vesicle complex, wherein the plurality of ultrasonic transducers applies an ultrasound wave to the microbubble-extracellular vesicle complex to form a focal point.

In the present disclosure, the plurality of ultrasonic transducers can apply an ultrasound wave to a microbubble-extracellular vesicle complex to form a focal point, whereby the microbubble-extracellular vesicle complex can be trapped within the formed focal point.

As used herein, the term "focal point" refers to a region formed in a three-dimensional space with the construction of an acoustic field by the plurality of ultrasonic transducers.

In an embodiment of the present disclosure, the plurality of ultrasonic transducers applies an ultrasound wave to the microbubble-extracellular vesicle complex at different time points to move the formed focal point to different positions, whereby the plurality of ultrasonic transducers can move the trapped microbubble-extracellular vesicle complexes along the positions of the focal point.

Therefore, the microbubble-extracellular vesicle complex driving system of the present disclosure can effectively deliver various drugs loaded to the microbubble-extracellular vesicle complex, such as DNA, RNA, anticancer compounds, and so on, to target sites.

In particular, therapeutic agents that may be loaded and administered with the present microbubble-extracellular vesicle complex include antibiotics, proteins, including antibodies, steroids, polynucleotides.

In certain aspects, the present microbubble-extracellular vesicle complex may be associated with anti-neoplastic or chemotherapeutic agents used to treat cancer in tumor therapy. For example, suitable chemotherapeutic agents for use with a present microbubble-extracellular vesicle complex include alkylating agents e.g. cisplatin, carboplatin, oxaliplatin, mechlorethamine, cyclophosphamide, chlorambucil, antimetabolites such as azathiopurine, mercaptopurine, plant alkaloids and terpenoids such as vinca alkaloids, podophyllotoxin and taxanes, topoisomerase inhibitors and antitumor antibiotics.

A better understanding of the present disclosure may be obtained via the following examples which are set forth to illustrate, but are not to be construed as limiting the present disclosure.

Preparation Example 1: Preparation of Microbubble

As microbubbles, Sonazoid™ from GE Healthcare was used. For a solution of Sonazoid™, Sonazoid™ in a powder formulation is mixed with an Annexin V-conjugated solution [0.1 M Hepes, 1.4 M NaCl, 25 mM $CaCl_2$ (pH 7.4)] instead of physiological saline.

Preparation Example 2: Preparation of Microbubble-Extracellular Vesicle Complex 2-1. Preparation of Cell Natural killer cells (NK-92) were purchased from ATCC (American Type Culture Collection) and cultured. Natural killer cells were cultured in MEM alpha (Thermo Fisher Scientific) containing 12.5% of fetal bovine serum (FBS; Corning), 12.5% of horse serum (HS; Sigma-Aldrich) and 1% of an antibiotic, based on the total volume thereof, and supplemented with 0.2 mM inositol (Sigma-Aldrich), 0.1 mM 2-mercaptoethanol (Sigma-Aldrich), 0.02 mM folic acid (Sigma-Aldrich), and 100 IU/mL interleukin-2 (IL-2; Miltenyi Biotec).

2-2. Isolation of Extracellular Vesicle

Natural killer cells (NK cells) are immune cells that are responsible for the first line in the body's immune system. NK cells are an important biomarker regulating immune inflammatory responses and can directly attack and kill abnormal cells, such as tumor cells, virus-infected cells, etc. However, the activity of NK cells is difficult to control due to versatile activation mechanisms therein. Particularly in a therapy for targeting solid cancer, NK cells are known to decrease in anticancer immune activity due to the low efficiency of access to cancer tissues.

Extracellular vesicles secreted from NK cells are as small as 50 to 150 nm in size and are known to easily circulate in vivo and be free of self-replication and cytotoxicity. Taking advantage of these characteristics, the nanosized, natural killer cell-derived extracellular vesicles succeeding to the genetic materials and information that natural killer cells retain can be used to improve efficiency of targeting to desired cancer sites and enhance anticancer immunity, thereby augmenting cancer cell killer effects. Thus, extracellular vesicles were separated from NK cells.

Extracellular vesicles present in sera act as a hinderance to the isolation of extracellular vesicles excreted from NK cells, so that the extracellular vesicles in each serum should be removed. In order to remove extracellular vesicles basically contained in each serum (bovine fetal serum and horse serum), the serum was centrifuged at 4° C. and 100,000×g for 18 hours. The extracellular vesicle-removed bovine fetal serum and horse serum was incubated at 37° C. for 3-5 days in a NK cell culture medium obtained in Preparation Example 2-1 under a 5% $CO_2$ condition.

After incubation, the supernatant was pooled and centrifuged at 300×g for 10 min. The cell pellet was removed, and the supernatant was centrifuged again at 2,000×g for 10 min for screening out cell debris and dead cells. Subsequently, centrifugation of the supernatant at 100,000×g for 30 min resulted in a medium containing extracellular vesicles, but not an apoptotic body.

The culture containing extracellular vesicles were concentrated into a ⅕ to 1/10 volume while molecules smaller than extracellular vesicles were removed therefrom using tangential flow filtration (TFF). The concentrated culture containing extracellular vesicles was centrifuged at 100,000×g and 4° C. for 90 min using an ultracentrifuge to give an extracellular vesicle pellet. The extracellular vesicle pellet was washed once with PBS (phosphate buffer saline) and suspended in about 1 mL of PBS.

2-3. Coupling of Microbubble-Extracellular Vesicle Complex

A coupling procedure between Sonazoid™ microbubbles and extracellular vesicles and a microbubble-extracellular vesicle complex are schematically depicted in FIG. 1.

A mixture of 200 μL of Sonazoid™ microbubble and 20 μL of biotinylated annexin V (Biolegend) was incubated at 4° C. for 15 min. Being dependent on calcium ions, annexin V binds specifically to phosphatidylcholine, which is a major ingredient in Sonazoid™ microbubbles. After 15 minutes of incubation, annexin V remaining unbound to Sonazoid™ microbubbles was removed by centrifugation at 100×g for 1 min and 200 μL of a new annexin V binding buffer was added.

To the solution of biotinylated annexin V-conjugated microbubbles was added 50 μL of a 1 mg/mL avidin solution, followed by incubated at 4° C. for 30 min. After 30 min of incubation, centrifugation at 100×g for 1 min removed the avidin that remained unbound, and 200 μL of an annexin V binding buffer was added to afford avidin-bound microbubbles.

In order to biotinylate the surface of the extracellular vesicle, sulfo-NHS-bound biotin (Thermo Fisher Scientific) was used to induce the formation of a stable amide bond with amino groups ($-NH_2$) of surface proteins on cells and vesicles.

First, sulfo-NHS-bound biotin was mixed and incubated with 200 μg of the extracellular vesicles at 4° C. for 30 minutes. After 30 min of incubation, the sulfo-NHS-bound biotin that remained unbound to the extracellular vesicle was removed by adding an excess of 100 mM glycine and centrifugation at 100,000 g for 90 minutes. The supernatant was removed and the biotinylated extracellular vesicles were suspended in 200 μL of an annexin V binding buffer.

The biotinylated extracellular vesicles and the avidin-bound microbubbles were mixed at a volume ratio of 1:1 and incubated at 4° C. for 30 min to induce bonding between the biotin on the extracellular vesicles and the avidin on the microbubbles. After 30 min of the incubation, the extracellular vesicles that remained uncoupled were removed by centrifugation at 100×g for 1 min. The pellet was suspended in 10-200 μL of an annexin V binding buffer to construct a microbubble-extracellular vesicle complex.

The reason why avidin was first with microbubbles and then with the extracellular vesicles is to increase convenience and yield. In order to remove excess avidin, centrifugation is required to be conducted at 100,000×g for 90 min when mixing avidin first with the extracellular vesicles, but only at 100×g for 1 min when mixing avidin first with the microbubbles.

If the microbubbles, the extracellular vesicle, and the avidin are mixed simultaneously, there may occur the problem that coupling is formed between the microbubbles and between the extracellular vesicles. Thus, avidin was first mixed with the microbubbles.

Figure 2A:
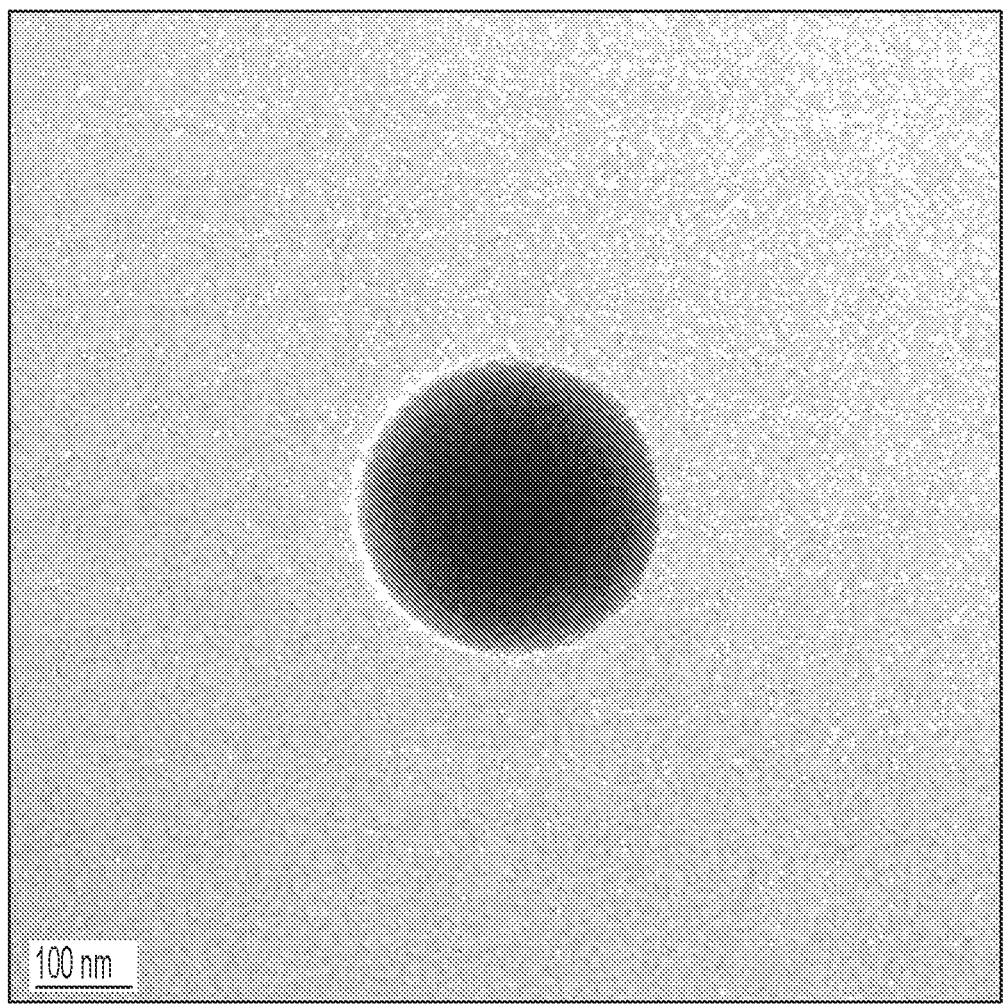
FIGS. 2A to 2D are a TEM image of the appearance of extracellular vesicles, a graph showing a size distribution of extracellular vesicles, and photographic images of immunoblotting results for extracellular vesicles.

Experimental Example 1: Characterization of Extracellular Vesicle 1-1. Appearance of Extracellular Vesicle In order to examine whether the extracellular vesicles were properly isolated, 1-10 μL of the extracellular vesicle solution was mounted on a formvar-coated TEM grid (TMA) and dried before observation under a transmitted electron microscope (TEM). A spherical morphology of the extracellular vesicle is depicted in FIG. 2a.

Figure 2B:
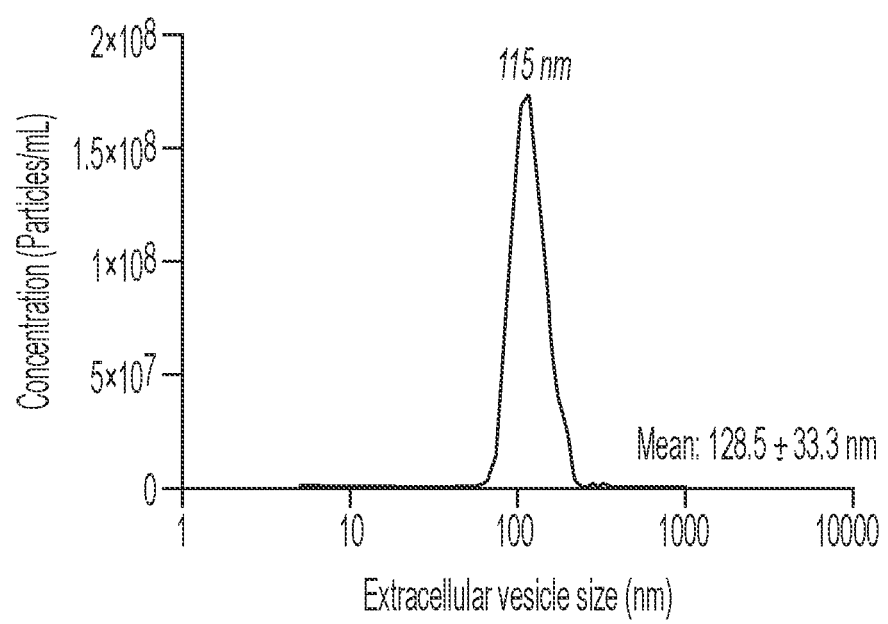

A size distribution of the extracellular vesicles obtained using a nanoparticle tracking analyzer (NTA) is depicted in FIG. 2B. As can be seen in FIG. 2b, the isolated extracellular vesicles were measured to have 128.5 nm±33.3 nm (Mean) and to fall within the size distribution of general extracellular vesicles about 130 nm in size.

1-2. Marker Expression of Extracellular Vesicle

Figure 2C:
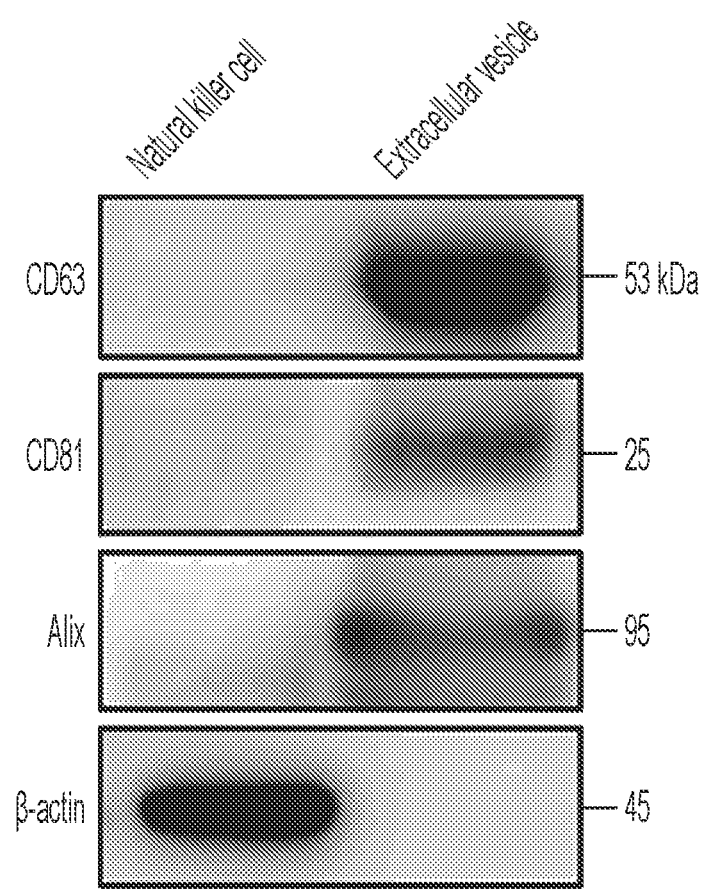
Figure 2D:
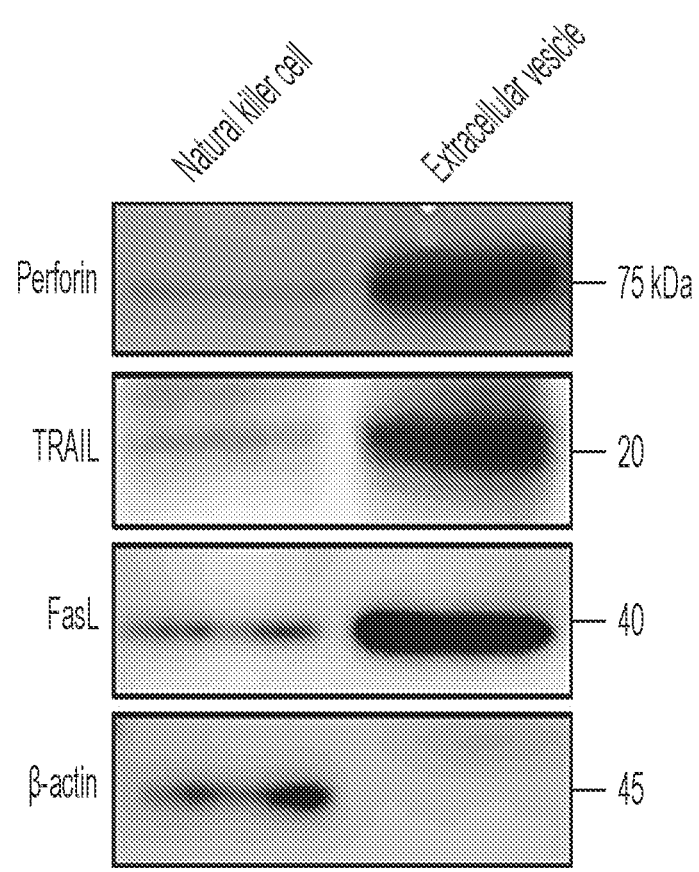

In order to examine whether the isolated extracellular vesicles expressed markers specific therefor and the same markers as in the mother NK cells, protein immunoblotting was performed, and the results are depicted in FIGS. 2C and 2D.

FIG. 2C shows the measurement of CD63, CD81, and Alix, which are the general markers expressed only in extracellular vesicles, with β-actin serving as a standard control. As can be seen in FIG. 2C, the extracellular vesicle-specific markers were absent in the mother NK cells, but detected in the extracellular vesicle. In addition, as shown in FIG. 2D, the expression of the same markers (perforin, TRAIL, and FasL) as in the mother NK cells demonstrated that the extracellular vesicles were derived from NK cells.

Experimental Example 2: Optimal Content Ratio of Microbubble and Annexin V

In order to determine an optimal content ratio at which as much annexin V as possible can be bound to microbubble, experiments were conducted with various amounts of annex V while a fixed amount of Sonazoid™ microbubbles was employed, as indicated in Table 1. The extracellular vesicles were stained with green fluorescent dye PKH67 (Sigma-Aldrich). The stained extracellular vesicles were reacted with various amounts of annexin V in the same manner as in Example 2 to afford microbubble-extracellular vesicle complexes.

Figure 3A:
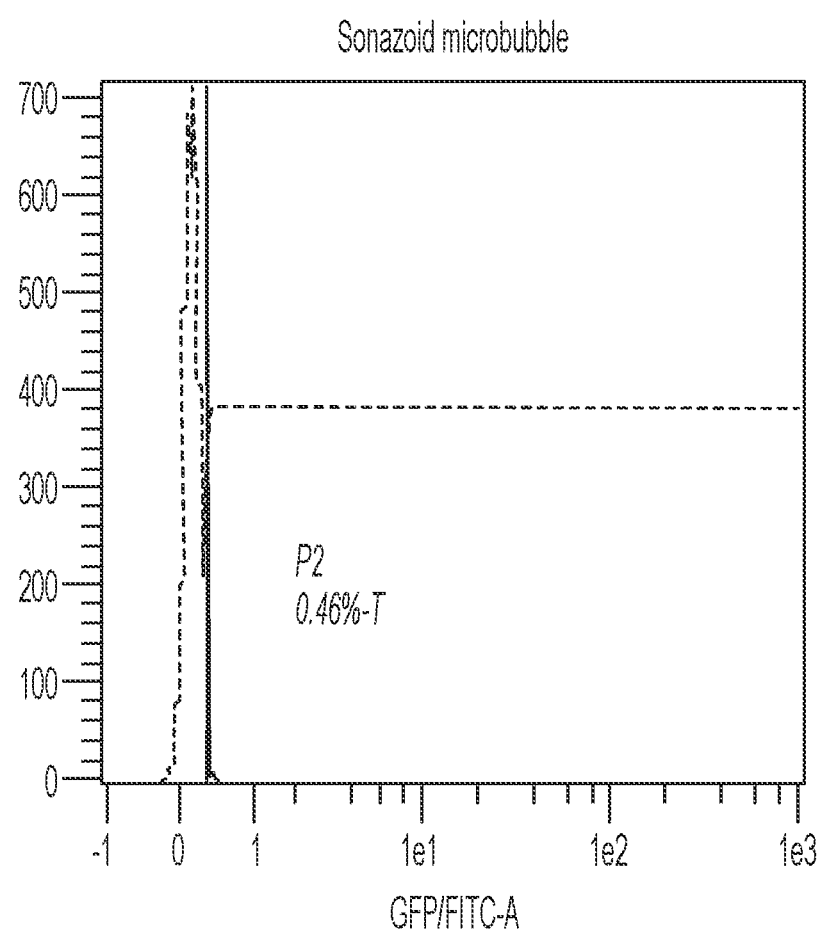
FIGS. 3A to 3E are FACS (Fluorescence activated cell sorter) plots of quantitative analysis for exosome conjugation according to concentrations of annexin V.
Figure 3B:
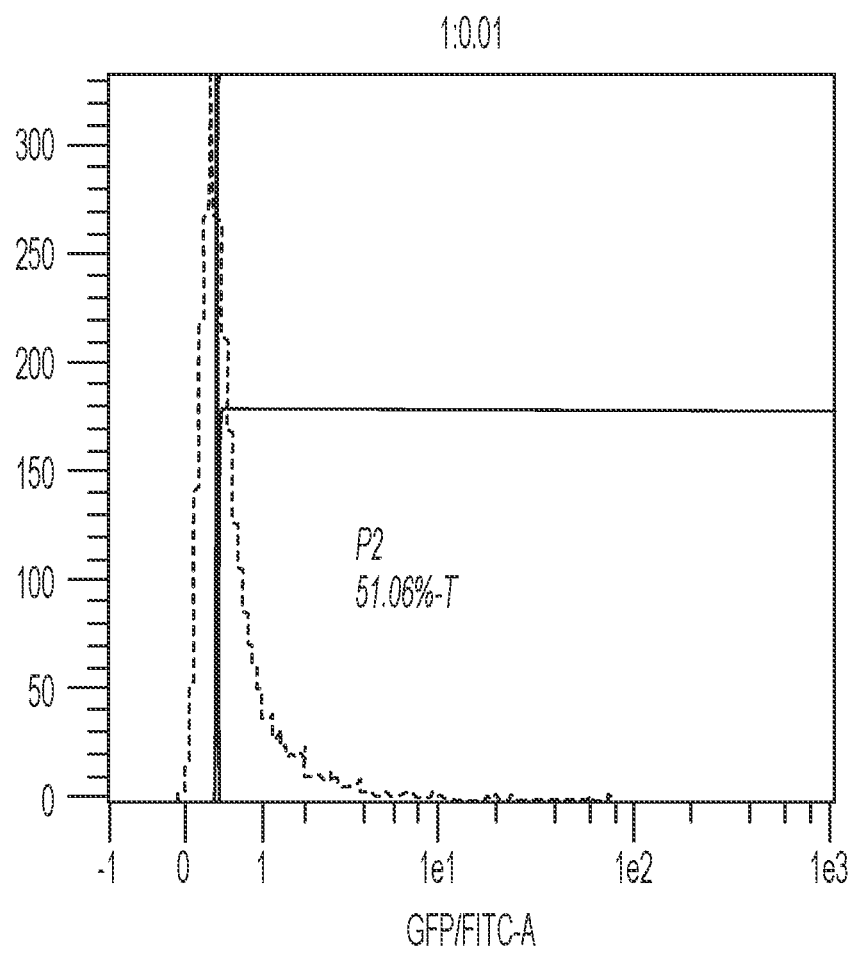
Figure 3C:
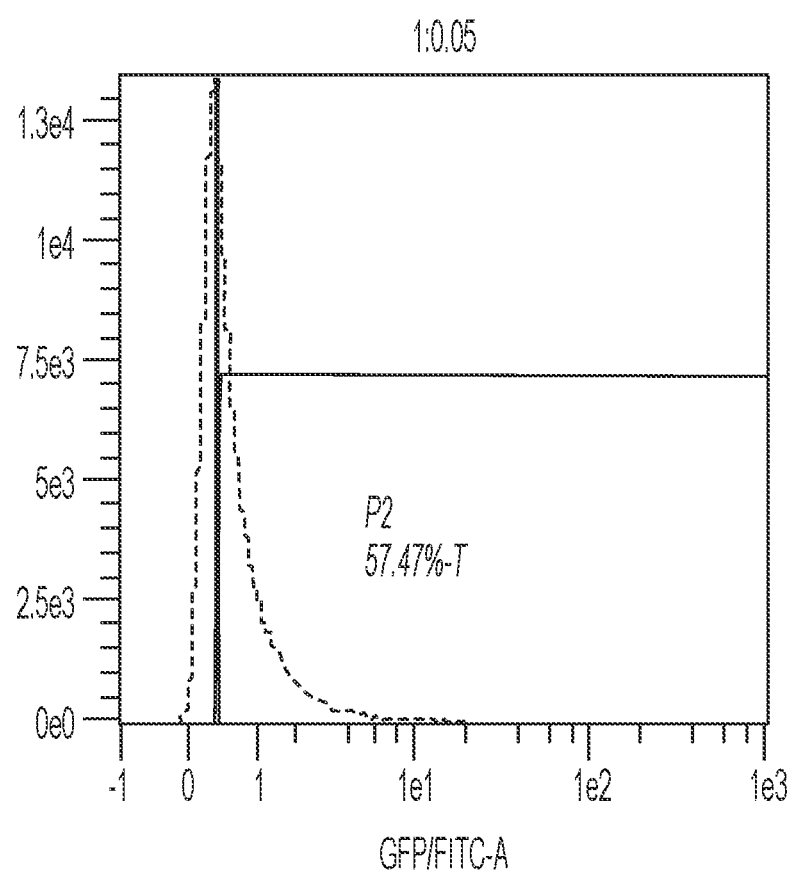
Figure 3D:
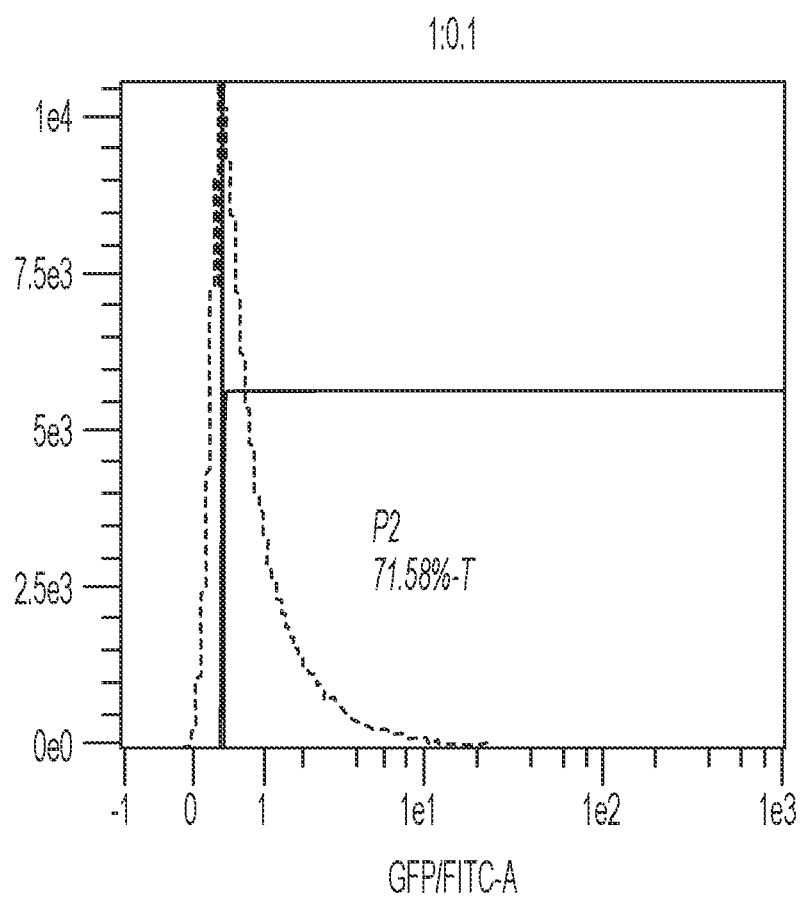
Figure 3E:
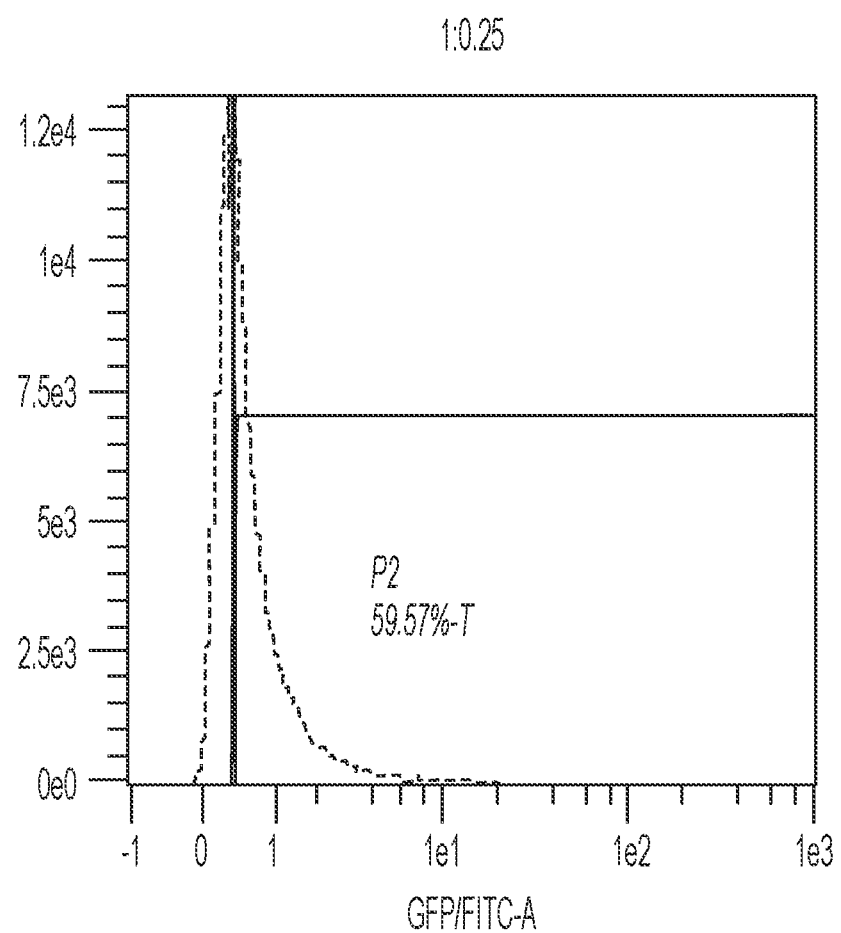
Figure 4A:
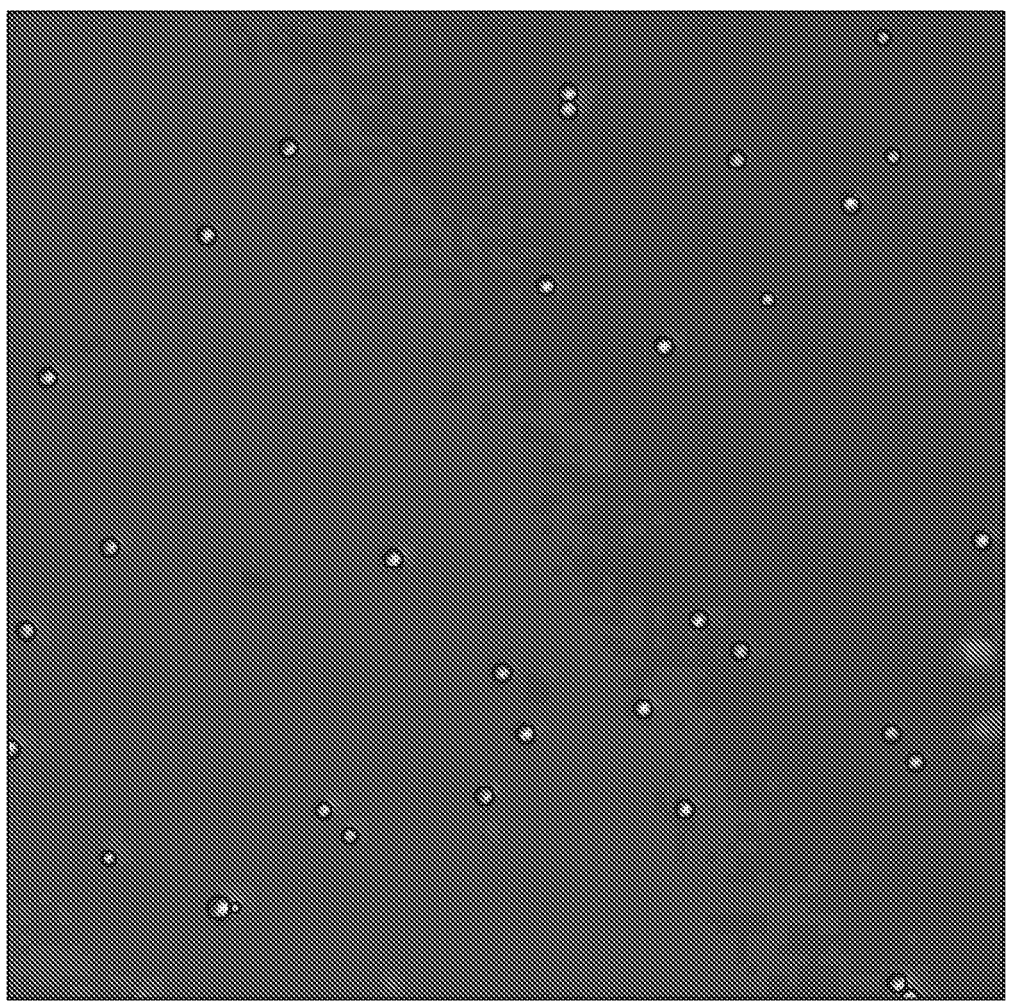
FIGS. 4A to 4E are confocal laser scanning microscopic images of exosomes conjugated with annexin V according to concentrations of annexin V.
Figure 4B:
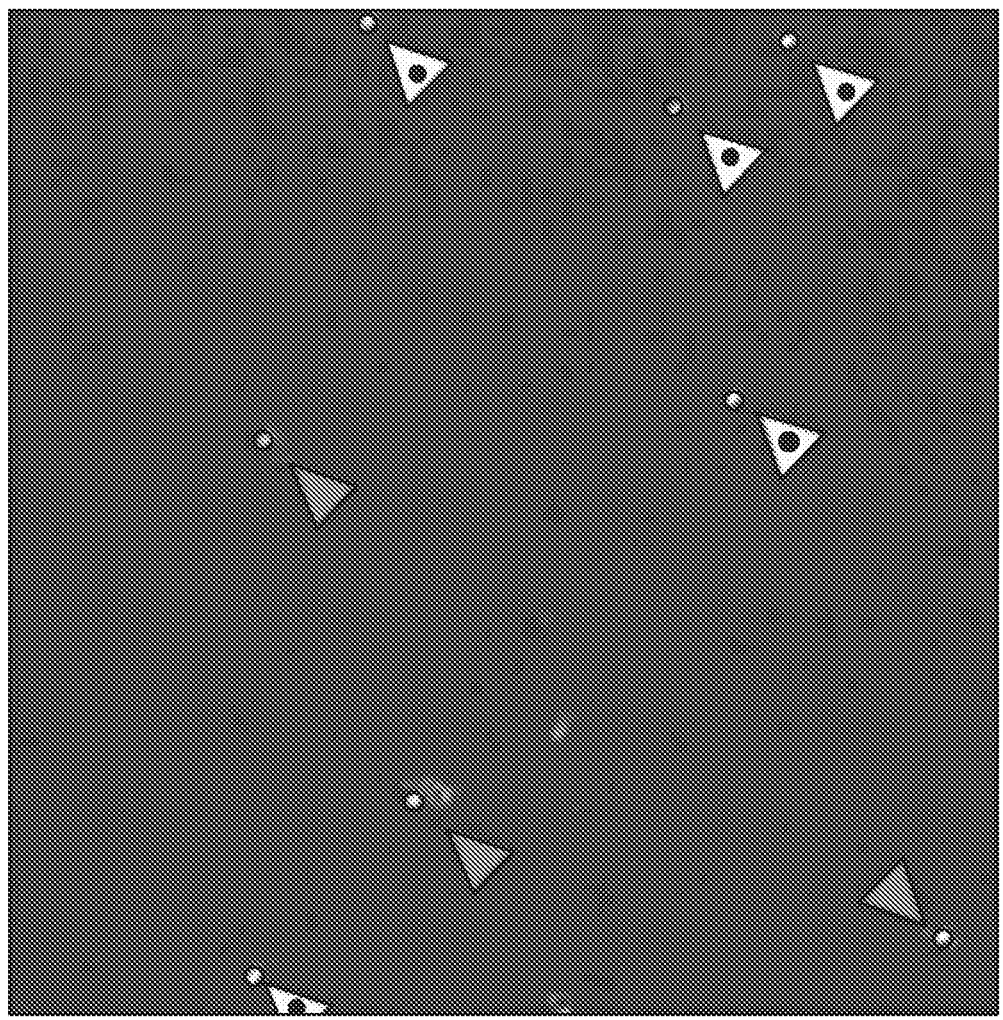
Figure 4C:
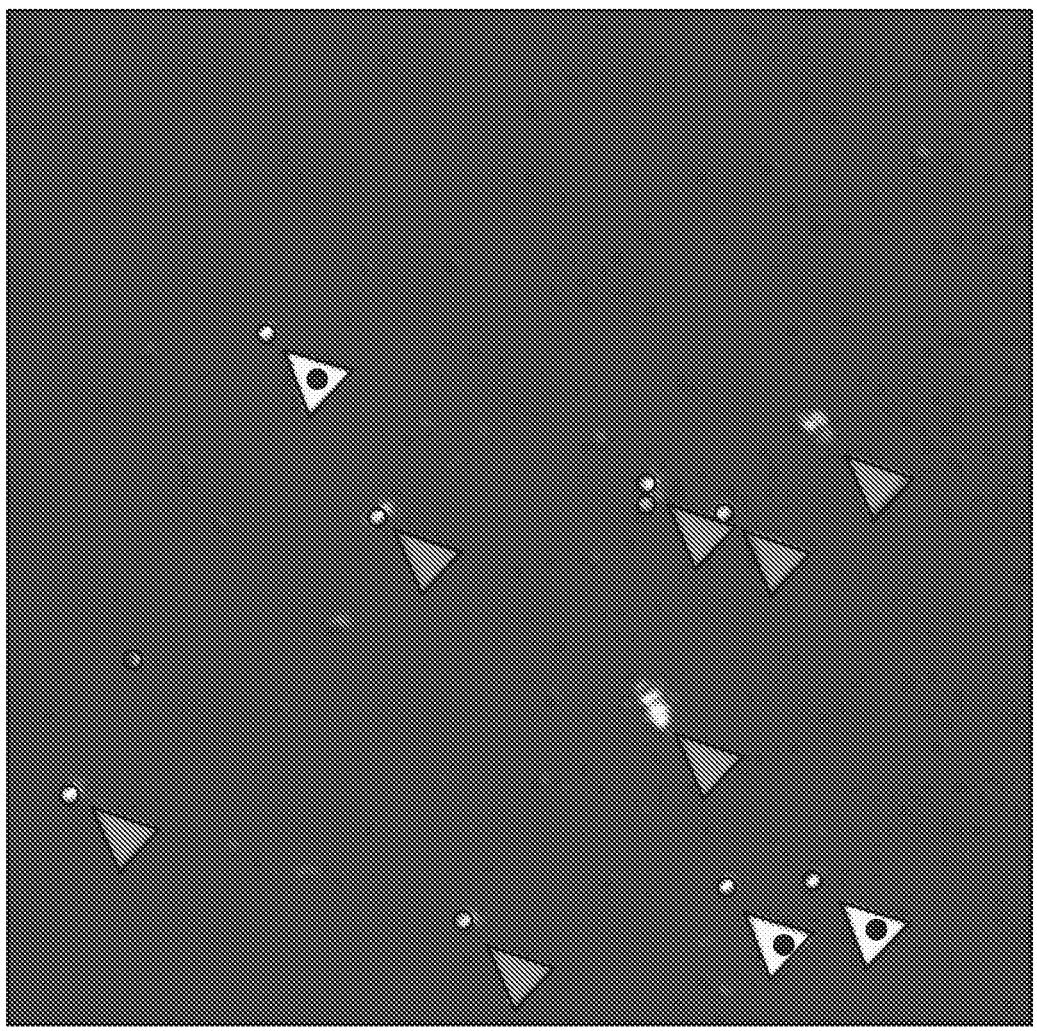
Figure 4D:
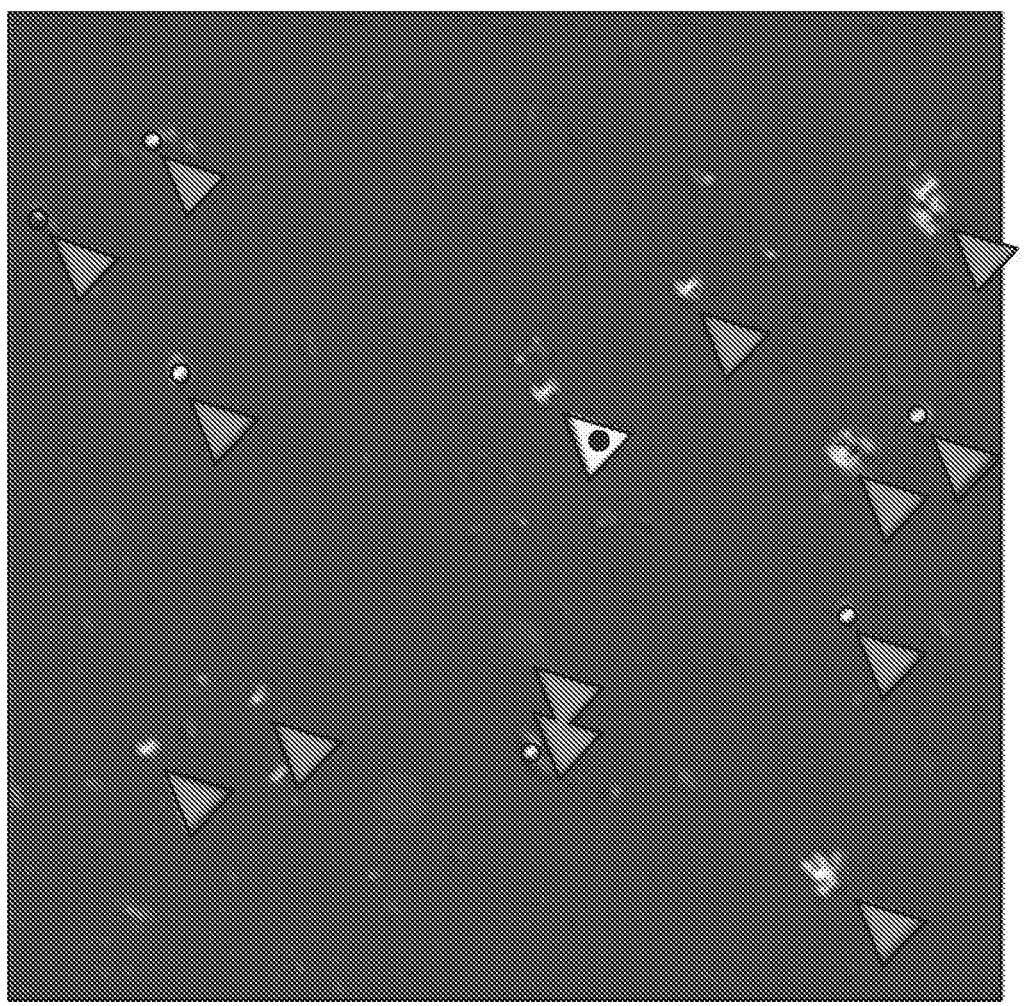
Figure 4E:
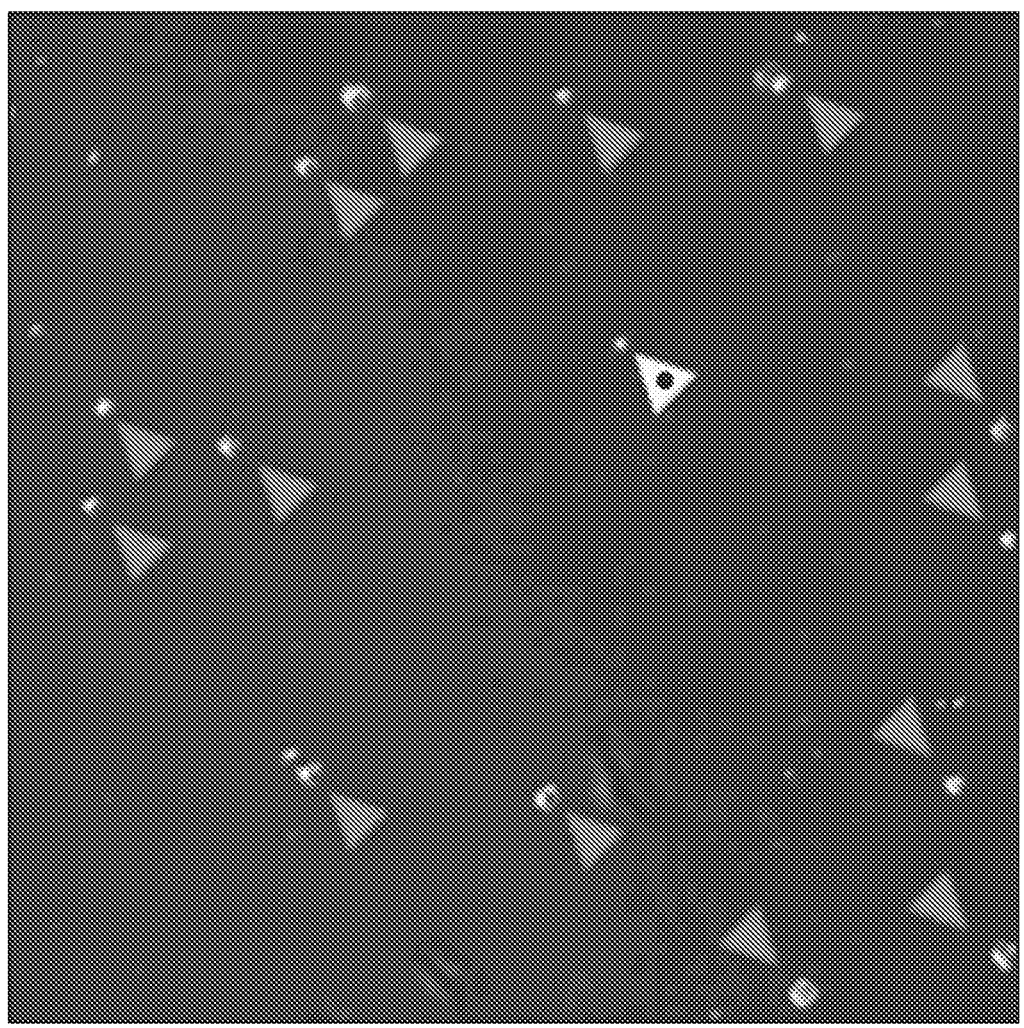

The complexes obtained were quantitatively analyzed for the microbubble-conjugated green fluorescence by flow cytometry. Sonazoid™ microbubbles were used to set a fluorescence reference. The fluorescence value of Sonazoid™ microbubbles themselves was measured to be 0.46%. The fluorescence values of the extracellular vesicles coupled to the microbubbles were measured according to the ratios of microbubble:annexin (1:0.01, 1:0.05, 1:0.1, 1:0.25 volume/volume) in Table 1. The results are depicted in FIG. 3a.

TABLE 1

|  | Microbubble (μL) | Annexin V (μL) | Volume ratio (v/v %) |
|---|---|---|---|
| Example 1 | 200 | 20 | 1:0.100 |
| Comparative Example 1 | 200 | 5 | 1:0.010 |
| Comparative Example 2 | 200 | 10 | 1:0.050 |
| Comparative Example 3 | 200 | 50 | 1:0.250 |

As shown in FIGS. 3A to 3E, the fluorescence value was measured to be 51.06% at a microbubble:annexin ratio of 1:0.010, 57.47% at a microbubble:annexin ratio of 1:0.050, 71.58% at a microbubble:annexin ratio of 1:0.100, and 59.57% at a microbubble:annexin ratio of 1:0.250, with a peak at the ratio of 1:0.100.

For qualitative analysis, the extracellular vesicles coupled to the microbubbles were measured according to the ratios of annexin V by confocal laser scanning microscopy. The results are depicted in FIGS. 4A to 4E. In FIGS. 4B to 4E, a dot was marked within an arrow head for a microbubble to which the extracellular vesicle was not coupled.

As can be seen in FIGS. 4A to 4E, the amount of the extracellular vesicles coupled to the microbubbles increased with an increase of the ratio of annexin V. At the reference volume ratio of 1:0.100 and at higher ratios, similar levels of the extracellular vesicles coupled to the microbubbles were detected, so that an optimal content ratio of microbubbles and annexin V was determined to be 1:0.100.

Figure 5A:
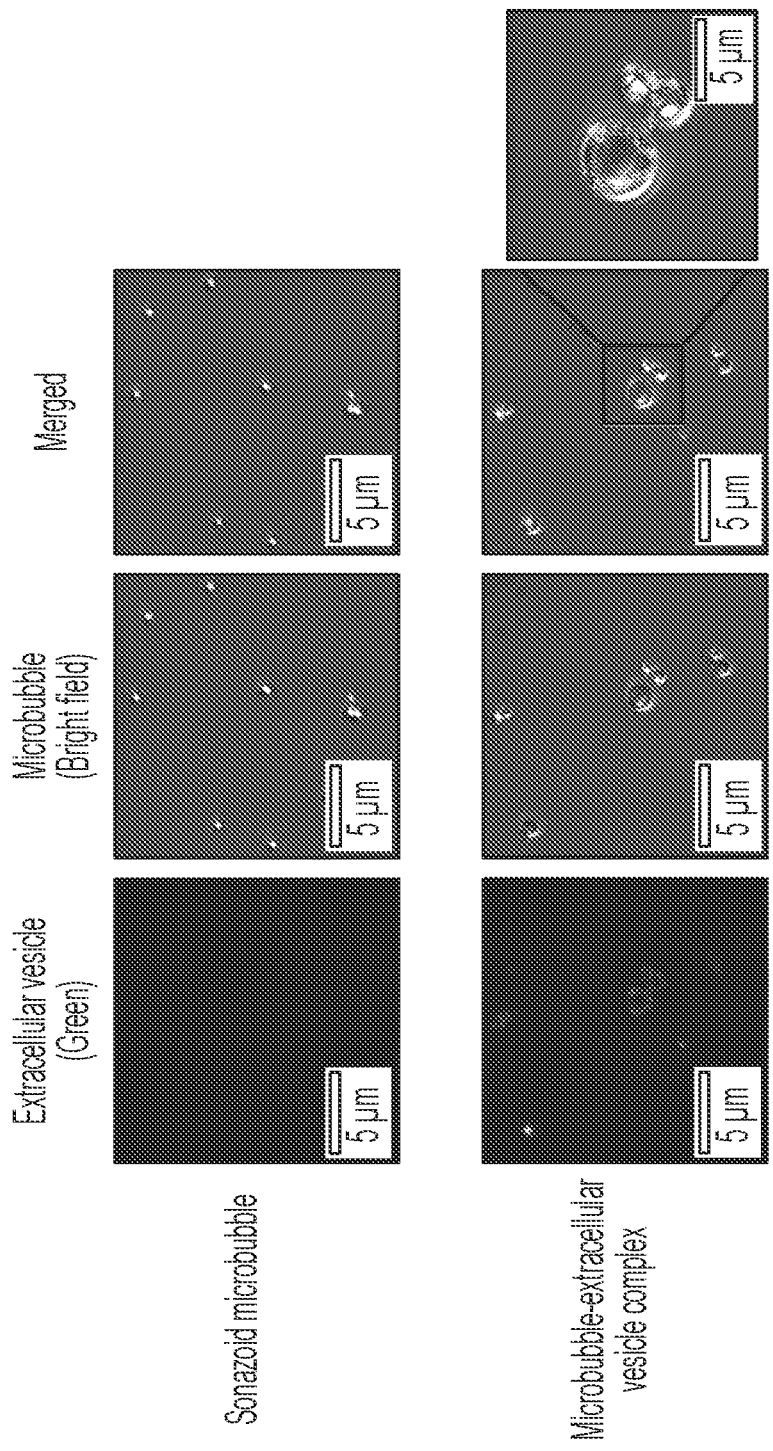
FIG. 5A shows images of microbubble-extracellular vesicle complexes according to content ratios (v/v) of the microbubbles and annexin V.

Experimental Example 3: Characterization of Microbubble-Extracellular Vesicle Complex Confocal laser scanning microscopic images of the microbubble-extracellular vesicle complexes constructed at the optimal content ratio indicated in Table 1 are depicted in FIG. 5A. As can be seen in FIG. 5A, extracellular vesicles conjugated with green PKH67 dye were observed around the microbubbles.

Figure 5B:
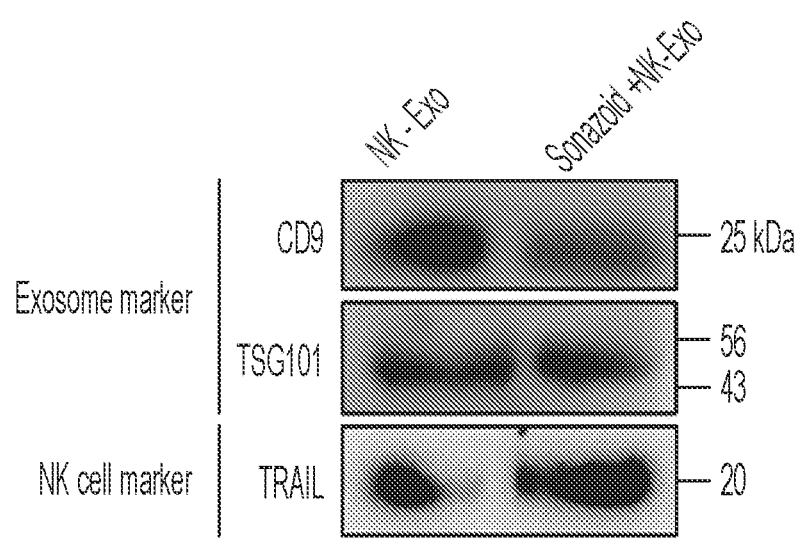
FIG. 5B is an image of immunoblots for markers specific for the microbubble-extracellular vesicle complex.

FIG. 5B shows immunoblotting results of measuring whether the extracellular vesicles coupled to the microbubbles retain markers specific therefor and an NK cell marker, simultaneously. As can be seen in FIG. 5B, the extracellular vesicles were well coupled to the microbubbles as the cell and vesicle markers (CD9 and TSG101) and the NK cell marker (TRAIL) were expressed.

Experimental Example 4: Ultrasound Image of Microbubble-Extracellular Vesicle Complex An examination was made to show whether the microbubbles complexed with the extracellular vesicles can perform their intrinsic function as an ultrasound contrast agent. As shown in A of FIG. 6, a tubular path with a diameter of 2 mm was made in an oblique pattern in a 1% agarose mold. Distilled water, the microbubbles, and the microbubble, microbubble-extracellular vesicle complex were each allowed to flow from the top to the bottom while ultrasonography was applied at an ultrasound intensity of 31-36 Hz. The results are shown in B of FIG. 6. As can be seen in B of FIG. 6, when the microbubbles or the microbubble-extracellular vesicle complex was flowed, ultrasonic waves were scattered and augmented, as opposed to the flow of distilled water. That is, the microbubble-extracellular vesicle complex was proven as an in vivo contrast medium.

Experimental Example 5:
Microbubble-Extracellular Vesicle Complex-Related 3D Driving 5-1. 3D Driving Device For use in driving the microbubble-extracellular vesicle complex, a hemispherical ultrasonic transducer array was fabricated. A limited number (16) of immersion probes (JAPAN PROBE) were employed. The array was designed and fabricated in a hemisphere form where the transducers were densely positioned with reference to the Y-axis parallel to the array as shown in FIG. 7, in order to increase the acoustic intensity at the focal position.

The individual ultrasonic transducers utilized had a resonance frequency of 1 MHz and a driving voltage of 60 Vpp. At the focal position, an acoustic radiation force capable of trapping a substance was generated. The focal position can move trapping positions to desired positions by using phase delay between individual transducer input signals.

5-2. 3D Driving

Figure 7:
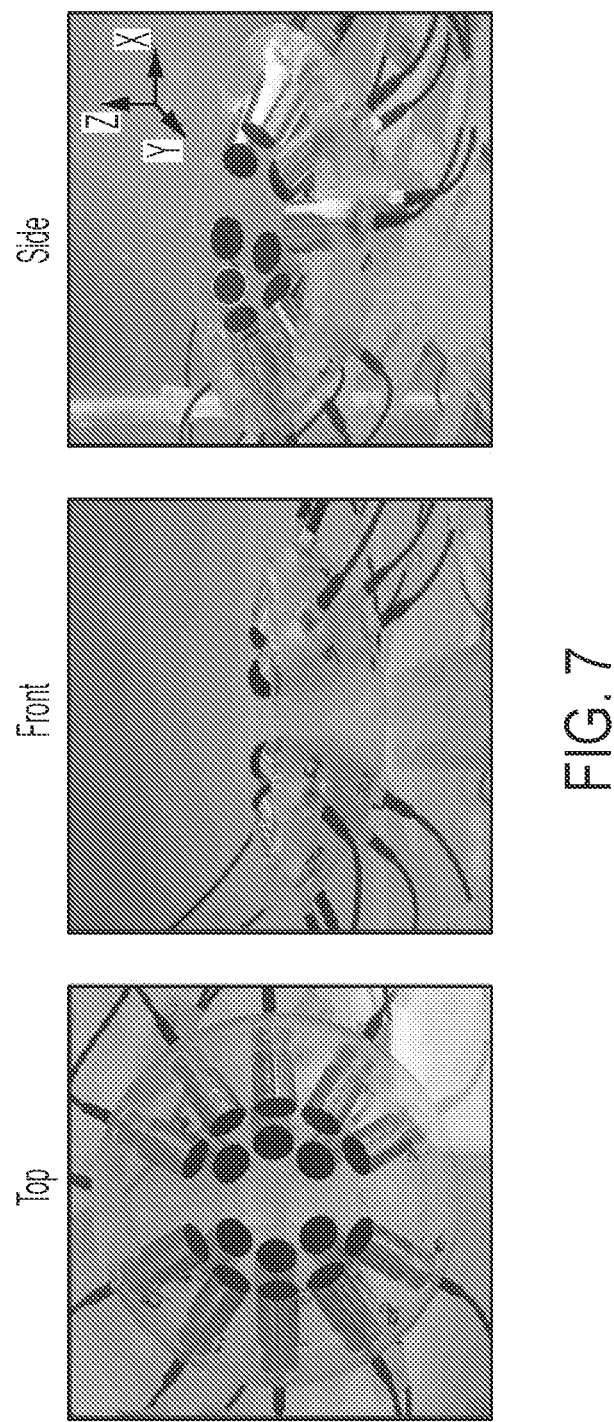
FIG. 7 shows photographic images of an ultrasonic driving device constructed for driving the microbubble-extracellular vesicle complex.
Figure 8:
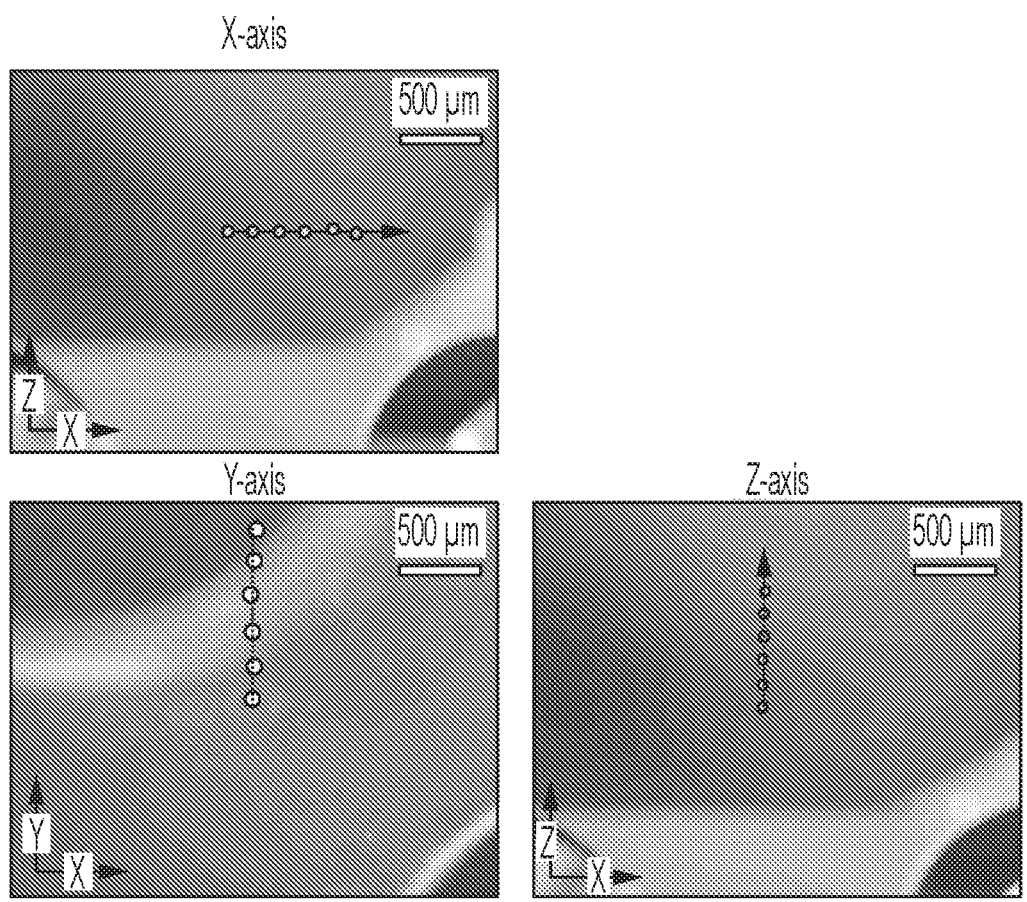
FIG. 8 shows images illustrating the movement of the microbubble-extracellular vesicle complex in x-, y-, and z-axis direction using the ultrasonic driving device.

A driving experiment using microbeads was carried out in order to examine whether the ultrasonic driving device of FIG. 7 can trap the complex at the focal position and move the same in a 3D mode. In consideration of the fact that aggregated multiple complexes should be derived in a real practice, beads with a size of 150 to 200 µm were employed. As shown in FIG. 8, the bead trapped at the focal position could be driven in the 3D mode of x, y, and z-axes.

In addition, an experiment was carried out in which polystyrene beads with a size of 10 µm, which are similar in physical properties to the microbubble-extracellular vesicle complex in which exosomes, a kind of extracellular vesicle contemplated in the present disclosure, were coupled to the microbubbles, were driven in a 20% gelatin chamber having a diameter of 3 mm.

Figure 9A:
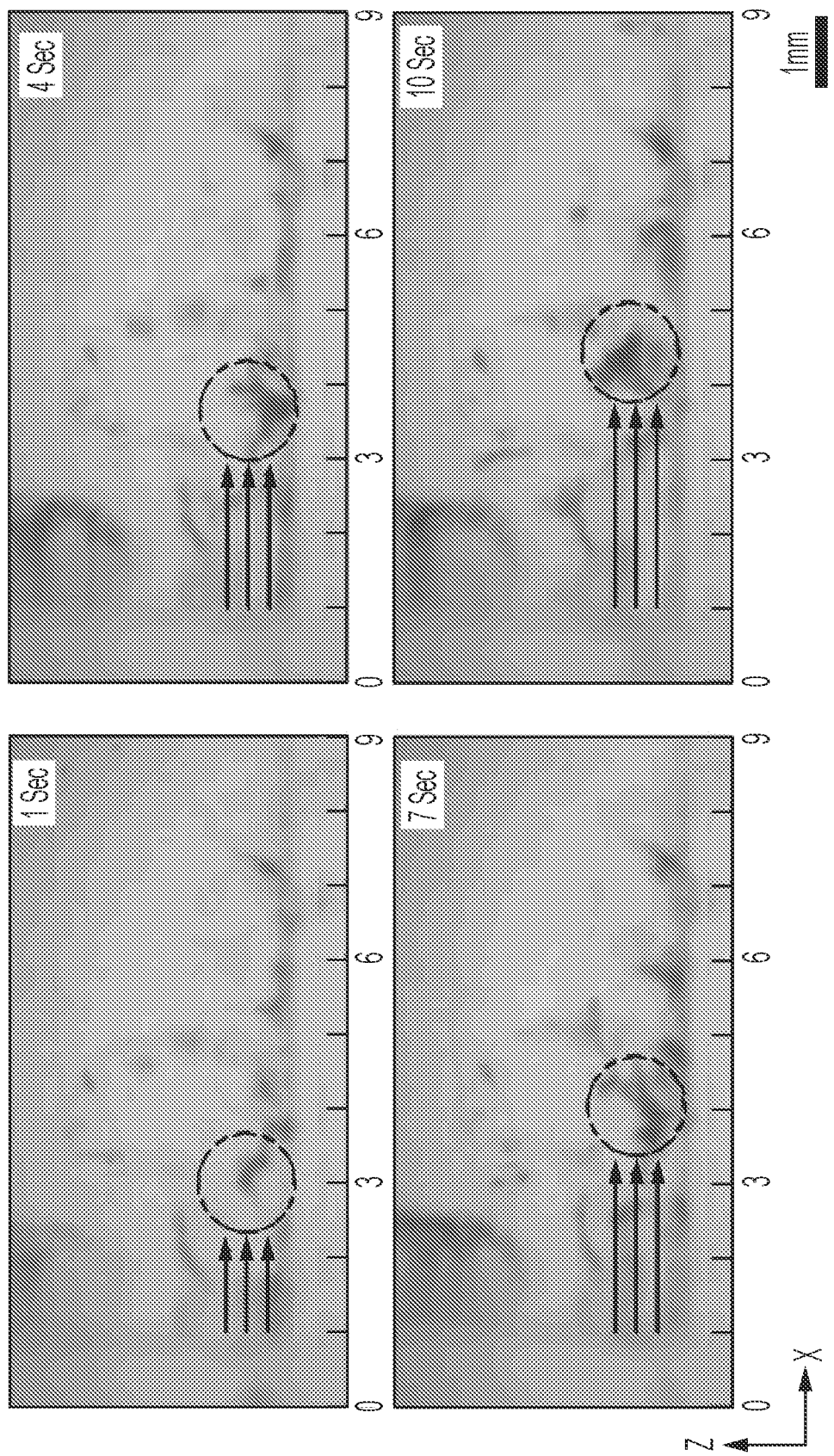
FIG. 9A shows images illustrating the unidirectional movement of polystyrene beads along the x-axis according to an experimental embodiment of the present disclosure.
Figure 9B:
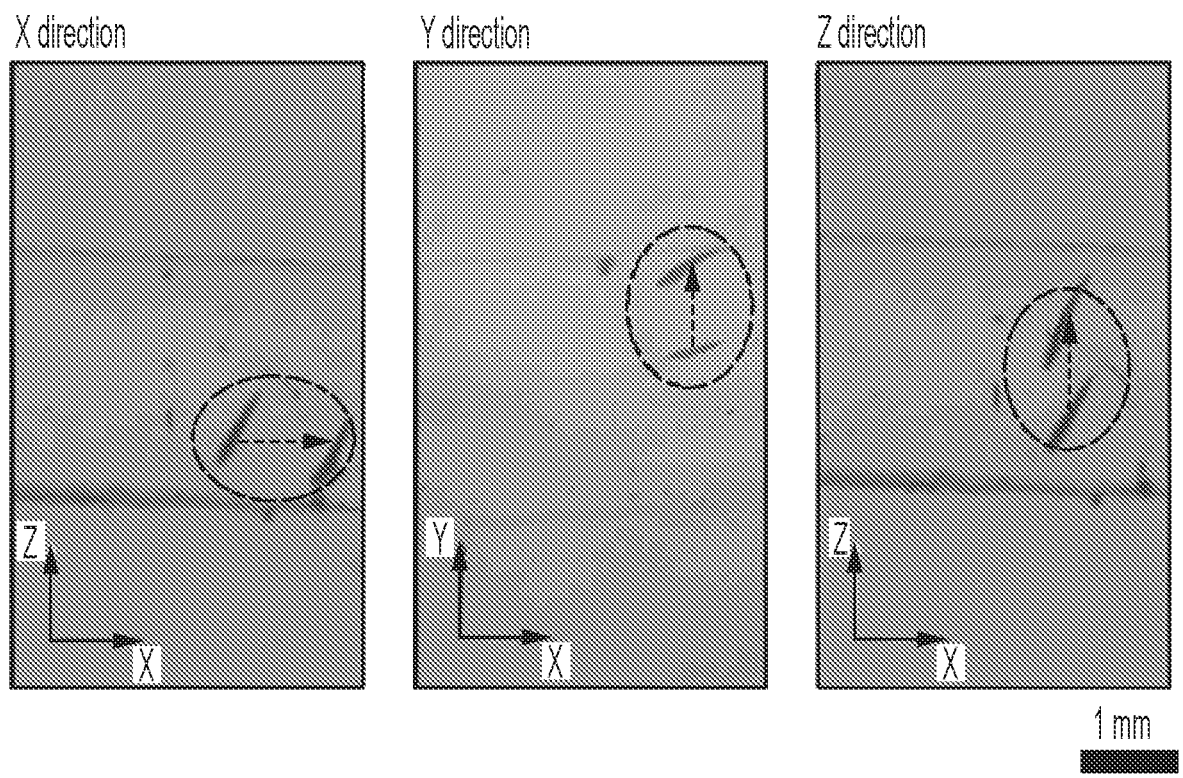
FIG. 9B shows images illustrating the 3D movement of polystyrene beads according to an experimental embodiment of the present disclosure.

Driving results of polystyrene beads are depicted in FIG. 9a for the x-axis unidirectional movement and in FIG. 9B for 3D movement.

As shown in FIG. 9A, the beads within the chamber could be moved in the x-axis direction using the "single beam" generated at the focal position.

As shown in FIG. 9B, it was possible to move the bead cluster in a 3D mode by trapping beads in the chamber by means of "twin trap" generable through the additional phase delay of "π" in the half of the transducers.

Example 6: In Vitro Anti-Tumor Effects of NK-Exo-Dox in HCC Hep3B Cells

Figure 10A:
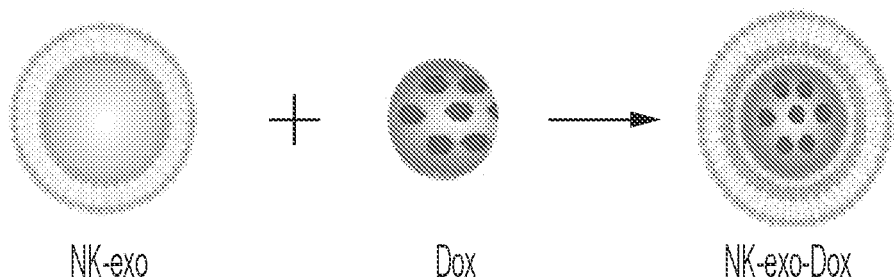
FIG. 10A: Schematic depiction of NK-exo-loaded Dox.
Figure 10B:
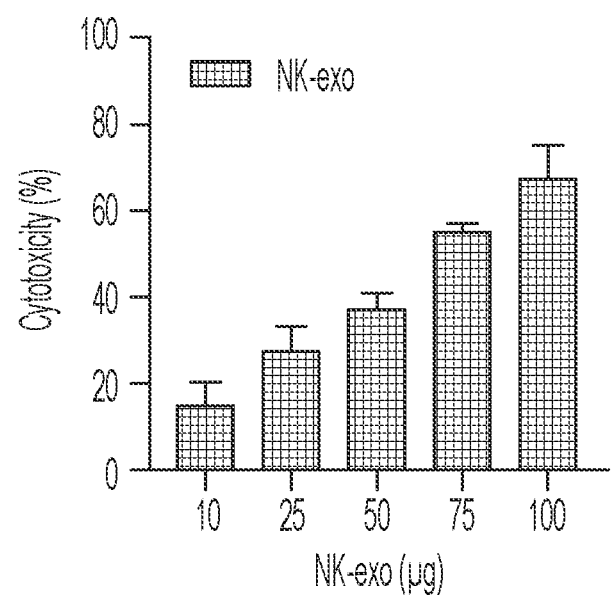
FIGS. 10B-C: Hep3B cells were treated with indicated different doses of NK-exo (B) and free Dox (C).
Figure 10C:
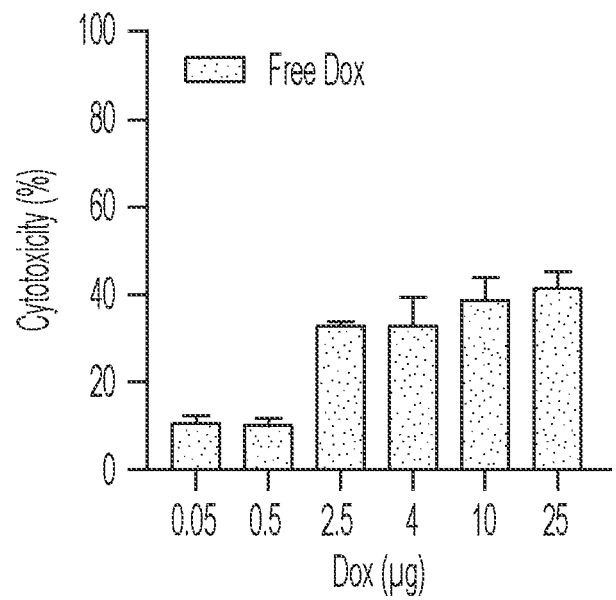
Figure 10D:
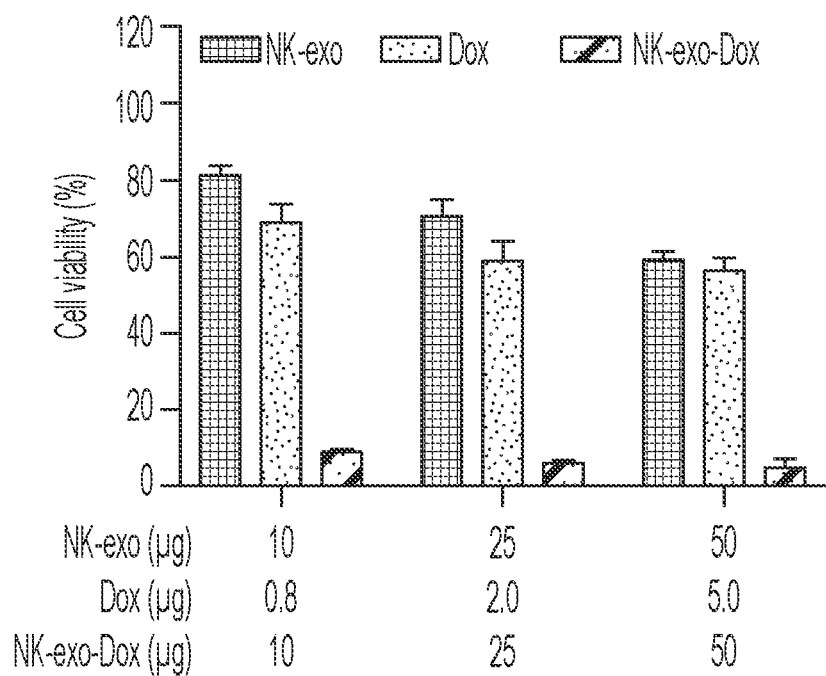
FIG. 10D: Hep3B cells were treated with indicated different doses of NK-exo, Dox, and NK-exo-Dox.
Figure 10E:
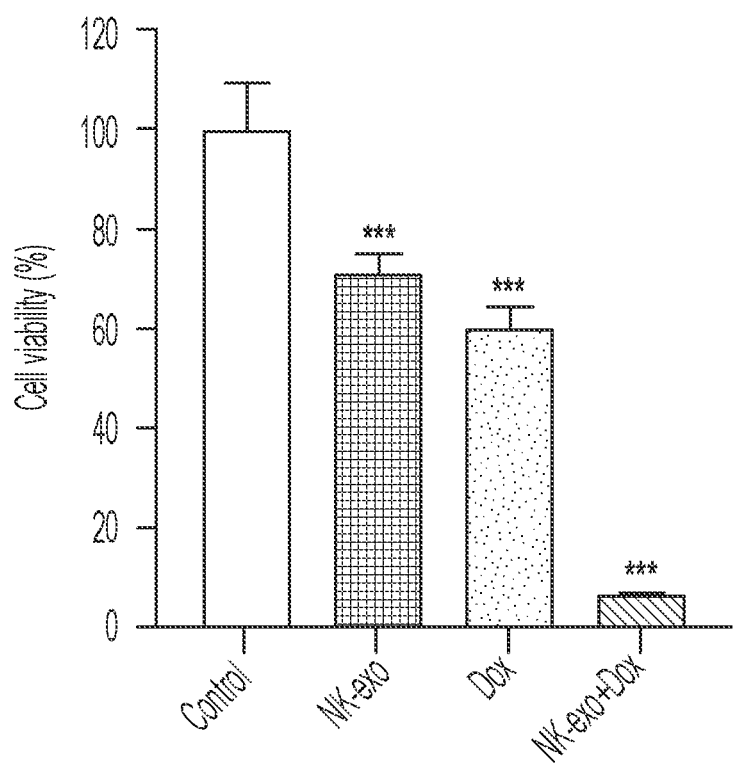
FIG. 10E: Hep3B cells were treated with NK-exo, Dox, and NK-exo-Dox.

FIG. 10A shows a schematic depiction of NK-exo-loaded Dox. Hep3B cells were treated with indicated different doses of NK-exo (FIG. 10B) and free Dox (FIG. 10C) for 24 h. LDH assay was performed as per the manufacturer's instructions to evaluate the cytotoxic effects of NK-exo and free Dox. The LDH levels were used to calculated the proportion of dead cells. Hep3B cells were treated with indicated different doses of NK-exo, Dox, and NK-exo-Dox. See FIG. 10D. The viability of Hep3B cells was measured as a metabolic activity using CCK-8 assay. See FIG. 10E. Hep3B cells were treated with NK-exo (50 µg), Dox (5 µg), and NK-exo-Dox (50 µg) for 24 h. The viability of Hep3B cells was measured as a metabolic activity using CCK-8 assay. Abbreviations: NK, natural killer cells; NK-exo, NK cell-derived exosomes; Dox, doxorubicin; NK-exo-Dox, NK-exo-loaded doxorubicin; HCC, hepatocellular carcinoma.

Figure 11A:
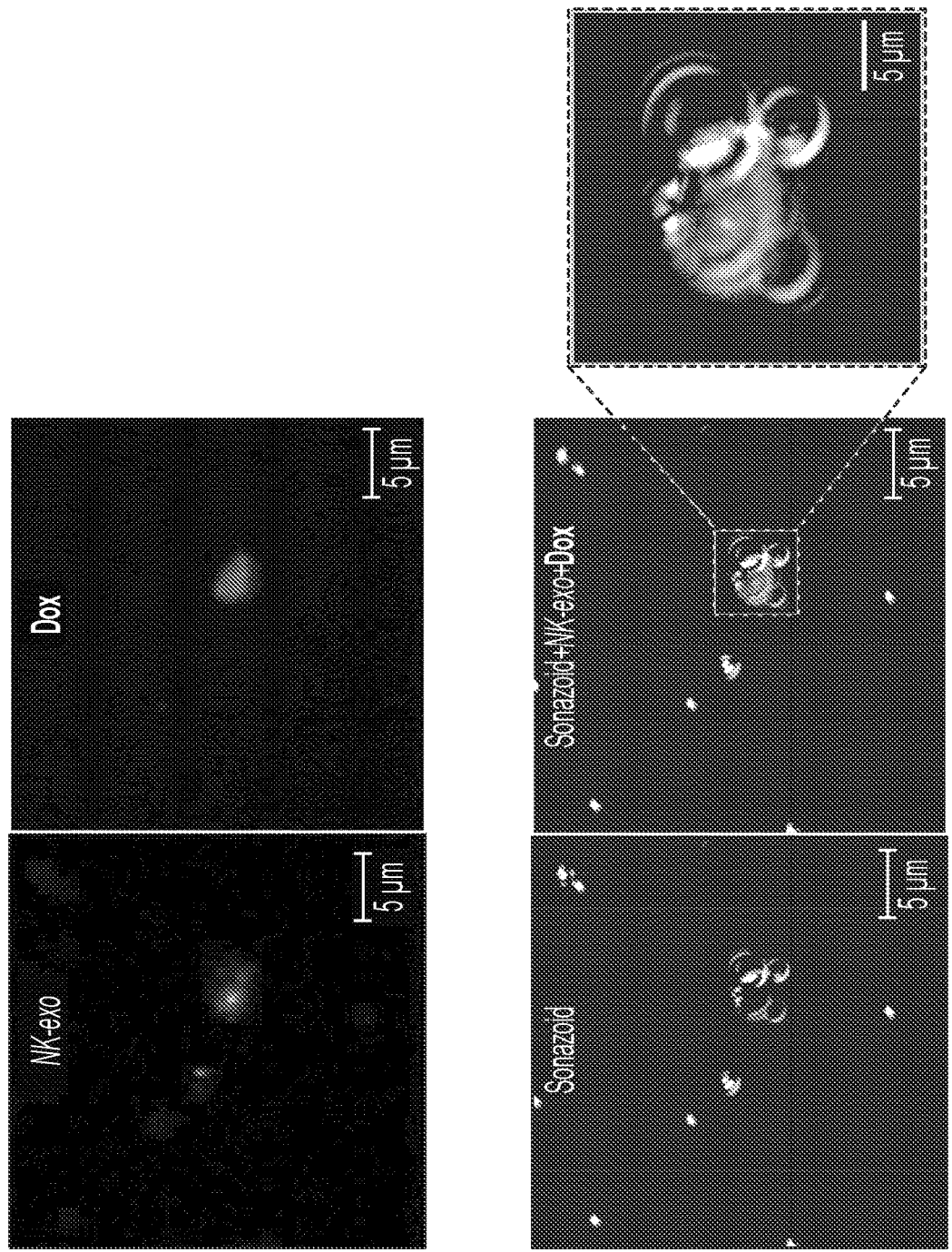
FIG. 11A: PKH67-labeled NK-exo (green), Dox (red), and sonazoid (white) were visualized via confocal laser scanning microscopy.
Figure 11B:
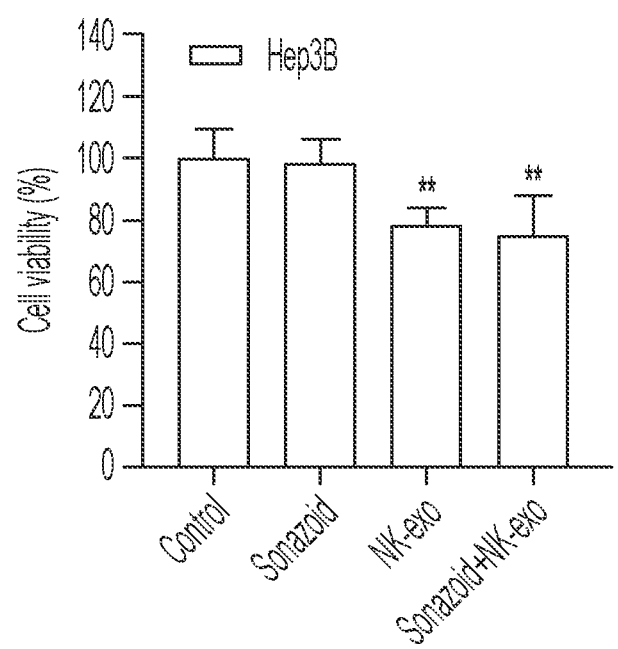
FIG. 11B: Hep3B cells were treated with NK-exo and Sonazoid.

Example 7: In Vitro Anti-Tumor Effects of Sonazoid+NK-Exo-Dox in HCC Hep3B Cells As shown in FIG. 11A, PKH67-labeled NK-exo (green), Dox (red), and sonazoid (white) were visualized via confocal laser scanning microscopy. Scale bars: 5 µm. (B) Hep3B cells were treated with NK-exo (20 µg), Sonazoid (20 µg) for 24 h. The viability of Hep3B cells was measured as a metabolic activity using CCK-8 assay. All data are expressed as mean±S.D. of at least three independent experiments. ***$p<0.001$ versus control group. Abbreviations: NK, natural killer cells; NK-exo, NK cell-derived exosomes; Dox, doxorubicin; NK-exo-Dox, NK-exo-loaded doxorubicin; HCC, hepatocellular carcinoma.

Example 8: Development of Exosome Carrier Acquisition Method for Enhanced Yield In order to determine the optimal isolation method of exosomes, quantitative analysis of exosomes isolated under various methods (ultrafiltration method(Filter), Ultra-centrifugal (UC), Tangential Flow Filtration method (TFF) was performed. It was confirmed that the amount of exosome isolation yield was significantly affected by the isolation method up to 3~8 times (FIG. 12A). Also, it was found that the UC and TFF method show a certain size of extracellular vesicle, which in the range of 100 to 200 nm (FIGS. 12B and C). Taken all, TFF method show the highest yield efficiency and a certain size uniformity (100~200 nm) of produced exosome.

Example 9: Cytotoxicity in Exosome in Human iPS Cell Derived Motor Neuron

Figure 13:
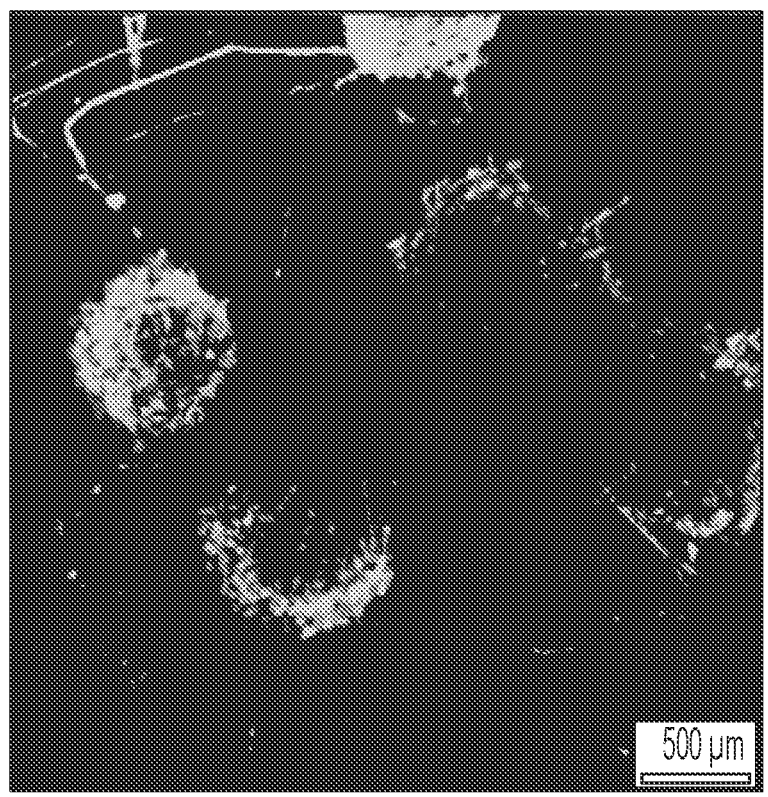
FIG. 13. Cytotoxicity in exosome in human iPS cell derived motor neuron was assess, FIG. 14 (includes FIGS. 14A-14B). Drug loading efficiency by selected methods was assessed.

To assess cytotoxicity of human schwann cell derived exosom, Live/Dead assay is conducted. The exosome were treated to human iPS cell derived motor neuron and livedead assay was performed 24 hr later. As a result, it is confirmed that exosome has no cytotoxicity and most of cell were survived after treating exosome. See FIG. 13.

Example 10: Drug Loading Efficiency

Figure 14A:
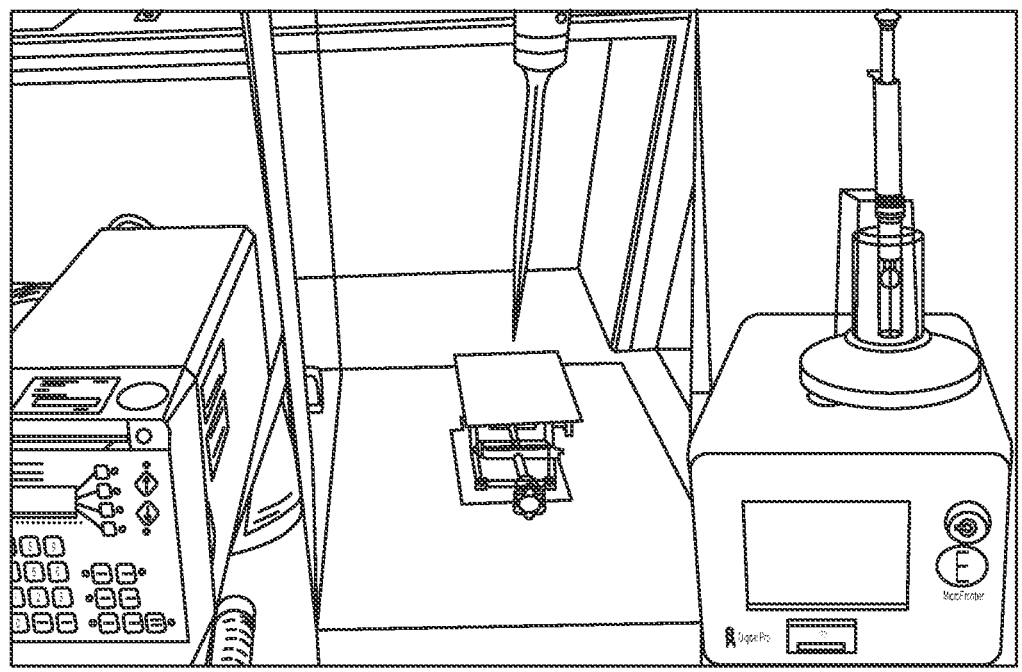
Figure 14B:
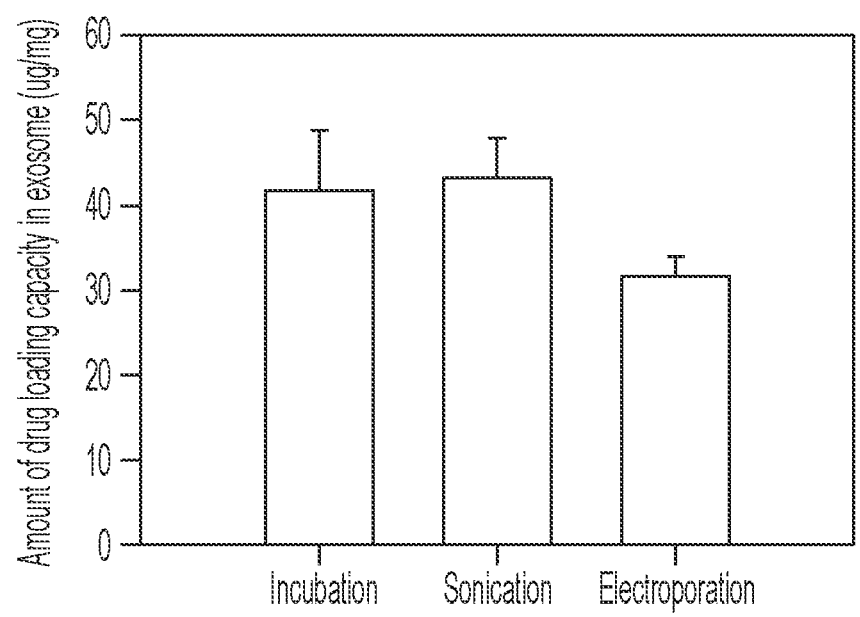

Drug loading efficiency was assessed by several methods: Incubation, Sonication, and Electroporation. In model system, loading of CKD504 (a drug for the treatment of peripheral neuropathy) was examined in the Schwann cell-derived exosome. CKD504 was loaded through three methods: Incubation, Sonication, and Electroporation. It was confirmed that the method using the tip sonicator was loaded with a higher amount of drug loading per unit exosome of 43.22 ug/mg compared to the 41.7 ug/mg incubation at 37 degrees C., and the 1400 V 20 ms pulse electroporation with 31.67 ug/mg. See FIG. 14.

What is claimed is:

1. A system for driving a microbubble-extracellular vesicle complex for treating hepatocellular carcinoma, the system comprising:
   a) a plurality of ultrasonic transducers wherein the plurality of ultrasonic transducers are configured to apply an ultrasound wave to the microbubble-extracellular vesicle complex to form a focal point, wherein the plurality of ultrasonic transducers are arranged hemispherically and consists of 16 immersion-type ultrasonic transducers, each having a diameter of 16 mm and a resonance frequency of 1 MHz;

b) a microbubble-extracellular vesicle complex; and
c) a therapeutic agent,
 wherein the microbubble is a gas-filled microsphere and comprises phosphatidylcholine, biotin, and annexin V;
 wherein the extracellular vesicle is derived from a natural killer cell (NK cell) and comprises biotin and N-hydroxysulfosuccinimide (sulfo-NHS);
 wherein the biotin of the microbubble is coupled to the biotin of the extracellular vesicle by avidin;
 wherein the therapeutic agent is doxorubicin;
 wherein the microbubble-extracellular vesicle complex exhibits anti-tumor activity against hepatocellular carcinoma or Hep3B hepatocellular carcinoma cell lines; and
 wherein the system is configured to deliver the doxorubicin to a target site by applying the ultrasound wave to rupture the microbubble and release the doxorubicin and cytotoxic proteins from the extracellular vesicle.

* * * * *